United States Patent
Zawada et al.

(10) Patent No.: US 11,622,752 B2
(45) Date of Patent: Apr. 11, 2023

(54) KITS FOR STABILIZATION OF CFDNA IN URINE SAMPLES

(71) Applicant: NephroSant, Inc., Brisbane, CA (US)

(72) Inventors: Robert Zawada, Redwood City, CA (US); Corinne Mark, South San Francisco, CA (US); Christopher Goulart, Franklin, MA (US)

(73) Assignee: NEPHROSANT, INC., Brisbane, CA (US)

( * ) Notice: Subject to any disclaimer, the term of this patent is extended or adjusted under 35 U.S.C. 154(b) by 0 days.

(21) Appl. No.: 17/709,310

(22) Filed: Mar. 30, 2022

(65) Prior Publication Data

US 2022/0219160 A1    Jul. 14, 2022

Related U.S. Application Data

(63) Continuation of application No. PCT/US2021/063937, filed on Dec. 17, 2021.

(60) Provisional application No. 63/127,122, filed on Dec. 17, 2020.

(51) Int. Cl.
*A61B 10/00* (2006.01)
*B01L 3/00* (2006.01)

(52) U.S. Cl.
CPC .............. *A61B 10/007* (2013.01); *B01L 3/50* (2013.01); *B01L 3/502* (2013.01); *B01L 3/56* (2013.01); *B01L 2200/026* (2013.01); *B01L 2200/04* (2013.01); *B01L 2200/0605* (2013.01); *B01L 2200/0689* (2013.01); *B01L 2200/16* (2013.01); *B01L 2200/185* (2013.01); *B01L 2300/042* (2013.01); *B01L 2300/044* (2013.01); *B01L 2300/046* (2013.01);
(Continued)

(58) Field of Classification Search
CPC .............. B01L 3/502; B01L 2200/026; B01L 2200/0605; B01L 2200/16; B01L 2200/185; B01L 2300/044; B01L 2300/046; B01L 2300/0672; B01L 2300/14; B01L 2400/049
USPC .......................................................... 422/512
See application file for complete search history.

(56) References Cited

U.S. PATENT DOCUMENTS

| 6,475,442 B1 | 11/2002 | Thompson et al. |
| 10,982,272 B2 | 4/2021 | Sarwal et al. |
| 10,995,368 B2 | 5/2021 | Sarwal et al. |

(Continued)

FOREIGN PATENT DOCUMENTS

WO    WO-2020141187 A1 *    7/2020    .............. A01N 31/02

OTHER PUBLICATIONS

Lee, E. Y. et al. (2020). "Comparison of Four Commercial Kits for Isolation of Urinary Cell-Free DNA and Sample Storage Conditions." Diagnostics 10:234, 1-10. (Year: 2020).*

(Continued)

*Primary Examiner* — Benjamin R Whatley
*Assistant Examiner* — Jacqueline Brazin
(74) *Attorney, Agent, or Firm* — Naira Simmons; FisherBroyles, LLP

(57) ABSTRACT

Disclosed here are kits comprising pre-packed stabilizing solutions for stabilizing combinations of biomarkers demonstrating sufficient accuracy and specificity for identifying kidney injuries. Such kits can be better adapted for sample collection at a subject's dwelling, thus easing the burdensome requirement of continuous monitoring for kidney injury.

18 Claims, 14 Drawing Sheets

(52) U.S. Cl.
CPC .................. *B01L 2300/0672* (2013.01); *B01L 2300/0832* (2013.01); *B01L 2300/14* (2013.01); *B01L 2400/049* (2013.01)

(56) References Cited

U.S. PATENT DOCUMENTS

| | | |
|---|---|---|
| 11,124,824 B2 | 9/2021 | Sarwal et al. |
| 2002/0055176 A1 | 5/2002 | Ray |
| 2002/0146677 A1 | 10/2002 | Augello et al. |
| 2003/0178328 A1 | 9/2003 | Williamson |
| 2005/0124965 A1* | 6/2005 | Haywood ........ A61B 5/150755 514/56 |
| 2005/0227269 A1 | 10/2005 | Lloyd, Jr. et al. |
| 2010/0079751 A1* | 4/2010 | Porat ....................... B01L 3/502 73/863.52 |
| 2014/0227687 A1 | 8/2014 | Horlitz et al. |
| 2021/0340610 A1 | 11/2021 | Sarwal et al. |
| 2022/0033892 A1 | 2/2022 | Sarwal et al. |

OTHER PUBLICATIONS

PCT/US2021/063937 International Search Report & Written Opinion dated Mar. 4, 2022.
Notice of Allowance in companion case, U.S. Appl. No. 17/709,340.
Office Action in companion case U.S. Appl. No. 17/709,348.

* cited by examiner

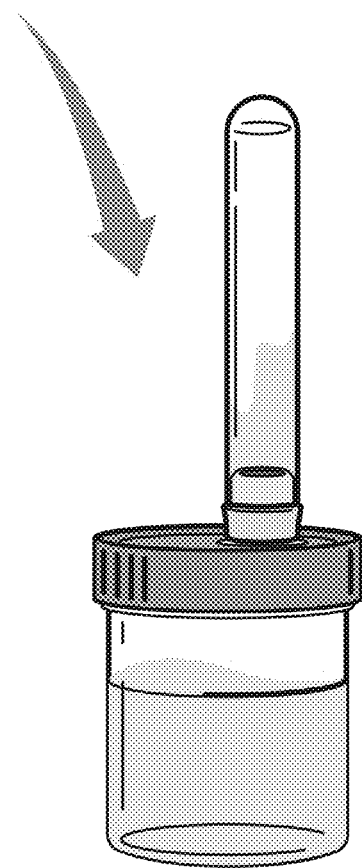
FIG. 7A
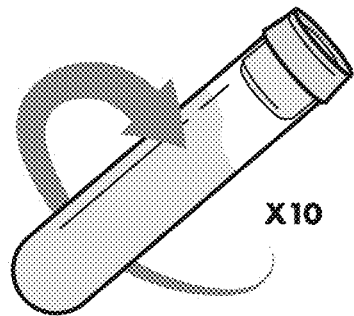
FIG. 7B
FIG. 7

KITS FOR STABILIZATION OF CFDNA IN URINE SAMPLES

CROSS-REFERENCE

The present application claims priority to International Patent Application No. PCT/US21/63937, filed on Dec. 17, 2021, which claims priority to U.S. Provisional Application Ser. No. 63/127,122, filed Dec. 17, 2020, the contents of both of which are hereby incorporated by reference in their entireties.

BACKGROUND

Analyte measurement in physiological fluids, e.g., urine or blood derived products, has important uses in a variety of applications, including clinical laboratory testing, home testing, etc., where the results of such testing play a prominent role in the diagnosis and management in a variety of disease conditions, including management of chronic conditions such as chronic kidney disease (CKD) and transplantation medicine.

According to the Centers for Disease Control and Prevention, kidney filtration begins to decrease by one percent every year after an individual's $40^{th}$ birthday. But sometimes that process can accelerate without noticeable signs. Chronic kidney disease (CKD)—in which the kidneys filter fewer wastes from the blood, causing them to build up in the body—can develop and proceed relatively symptom-free until your kidneys are badly damaged.

There is a critical unmet need for improved non-invasive diagnosis for the management and treatment of chronic conditions such as chronic conditions and organ transplantation.

SUMMARY

In some aspects, the disclosure provides a kit for the stabilization of a urine sample from a subject comprising: a vacutainer cup for the collection of the urine sample from the subject, the vacutainer cup having an inner protrusion functionally connected to a piercing hollow channel; and at least one urine sample collection tube having a volume of a pre-packaged solution or a pre-packaged powder for stabilizing at least one analyte in the urine sample, whereby the at least one urine sample collection tube has a top configured to form a suction vacuum when pierced by the piercing hollow channel. In preferred embodiments the analyte is a cell-free nucleic acid, protein, or both. In other embodiments, the analyte can be a cellular nucleic acid, e.g., mRNA, In most preferred embodiments the analyte is stable for at least 5 days at room temperature, including temperatures up to 86° F. The pre-packaged stabilizers in the collection tube can be provided in solution form or in powder form. Alternatively, the pre-packed solution can be also be sprayed onto the sides of the collection tube. These stabilizers are preferably used for stabilizing the cell-free nucleic acid in the urine sample, including methylated cell-free DNA, and the total protein in the urine sample and generally comprise formaldehyde, a formaldehyde quenching solution, a chelator and an agent that inhibits bacterial growth. In certain instances the kit comprises a second urine sample collection tube, also comprising pre-packaged stabilizers. The second urine collection sample generally comprises, a polyol, a protein crowding stabilizer, and a chelator. In most preferred cases, the stabilizers in the second tube are specifically designed to stabilize at least one additional biomarker, and the at least one additional biomarker is distinct from the cell-free DNA. In some cases, the cell-free DNA is not stable in the stabilizer used to pre-package the second stabilizer tube. The second urine sample collection tube may comprise a volume of a second pre-packaged solution or an amount of a pre-packaged powder for stabilizing at least one additional biomarker. In some cases, the second pre-packaged solution is for stabilizing an inflammation marker in the urine sample, such as CXCL10 or CXCL9. In other cases, the second pre-packaged solution is for stabilizing an apoptotic marker in the urine sample, such as clusterin. In other cases, the second pre-packaged solution is for stabilizing a metabolite in the urine sample, such as creatinine, and one or more dimethyl arginines (ADMA/SDMA). In most preferred cases, the second stabilizing solution is effective at stabilizing an inflammation marker, an apoptotic marker, or a metabolite.

Preferably, the kit further comprises an envelope, a box, or a bag for shipping one or more urine sample collection tube(s) after urine collection via a courier service, all of which may be pre-addressed—optionally with postage pre-paid—for postage to a urine analysis laboratory via the courier. In instances where the urine collection tube is pre-packed with a solution, the volume of the pre-packaged solution may ranges from 0.5 milliliters to 4 milliliters, preferably providing for a 5-fold dilution of the urine sample in order to achieve a desirable concentration ratio of stabilizer/urine. Specifically, the urine sample collection tube may be a 5 milliliter collection tube, a 10 milliliter collection tube, or a 12 milliliter collection tube all of which can be pre-packed with a solution or a powder that provides for a suitable final concentration of urine to stabilizer ratio. Alternatively, the pre-packed solution can be also be sprayed onto the sides of the collection tube.

The vacutainer cup itself is specifically designed for the collection of the urine sample from the subject. For instance, in many cases, the piercing hollow channel may not be suitable for a blood draw. Further, the stabilizer may not contain heparin or sodium fluoride (NaF), as it is not designed for a blood draw. Rather, the stabilizer solution may comprise a nuclease inhibitor in a concentration sufficient to inhibit nucleases in the urine sample. Further, the stabilizer solution may comprise a formaldehyde donor, a quencher, and a chelator in a concentration sufficient to inhibit cell lysis and to inhibit nucleases in the biofluid sample. Alternatively, the solution may comprise a chelator, a polyol, and sodium azide in a concentration sufficient to inhibit cell lysis and to inhibit nucleases in the biofluid sample.

In many cases, the status of an organ of the subject is being monitored with a kit of the disclosure. Specifically, in preferred embodiments the subject has, or is suspected of having organ injury. For instance, the subject may use a kit of the disclosure to monitor the status of a surgical procedure, such as in cases where the subject received an organ transplant and is being monitored for potential rejection of the allograft. In such cases, the subject may receive a kit with two urine collection tubes, where the first urine collection tube is configures to stabilize cell-free nucleic acid markers in the urine and the second tube is configured to stabilize, for example, one or more of an inflammation marker, an apoptotic marker, or a metabolite in the urine sample. In other cases, the subject may have been ill, such as a subject who has recovered from Sars-CoV-2. In such instances, the subject may receive a kit with one tube for collection and monitoring of a cell-free DNA marker that could reflect injury caused by the virus, such as injuries caused by low oxygenation of the kidney. In preferred cases, the kit further comprises instructions for using the same. In most preferred cases, the instructions provide guidance for a subject that has either received an organ transplant or is afflicted with chronic kidney disease (CKD) on how to use the kit.

In some aspects, the disclosure provides a method for stabilizing a urine sample of a subject, the method comprising: providing, by the subject, a urine sample in a vacutainer cup having an inner protrusion functionally connected to a piercing hollow channel; contacting, by the subject, at least one urine sample collection tube having a volume of a pre-packaged solution or a pre-packaged powder for stabilizing at least one analyte in the urine sample with the inner protrusion of the vacutainer cup, whereby the at least one urine sample collection tube forms a suction vacuum when piercing the piercing hollow channel, whereby the at least one urine sample collection tube suctions an amount of urine from the vacutainer cup to provide a collected urine sample; and remitting, by the subject, the collected urine sample to a laboratory for analysis.

Accordingly, disclosed herein are kits and methods for collecting a urine sample at a location, such as a subjects dwelling, and stabilizing solutions that support a subsequent analysis complex multivariate analysis of biomarkers from the subject.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1 illustrates two urine sample collection tubes of different sizes 101 and 103 pre-packed with suitable stabilizer solutions contained within each tube by a top 102 and 104, a lid 105 of a vacutainer cup having an inner protrusion with screw ridges that can functionally connect to the loose piercing hollow channel 106.

FIG. 2 illustrates two urine sample collection tubes of different sizes 101 and 103 having rubber tops 102 and 104, an unassembled vacutainer cup having a lid 105 with an inner protrusion and a cup 107.

FIG. 7 (FIG. 7) illustrates suction of the urine sample by the vacutainer and inversion of the sample for mixing. FIG. 7A illustrates the insertion of a urine collection tube into a vacutainer. FIG. 7B illustrates the inversion of the urine collection tube back-and-forth repeatedly for a sufficient number of times.

INCORPORATION BY REFERENCE

Figure 1:
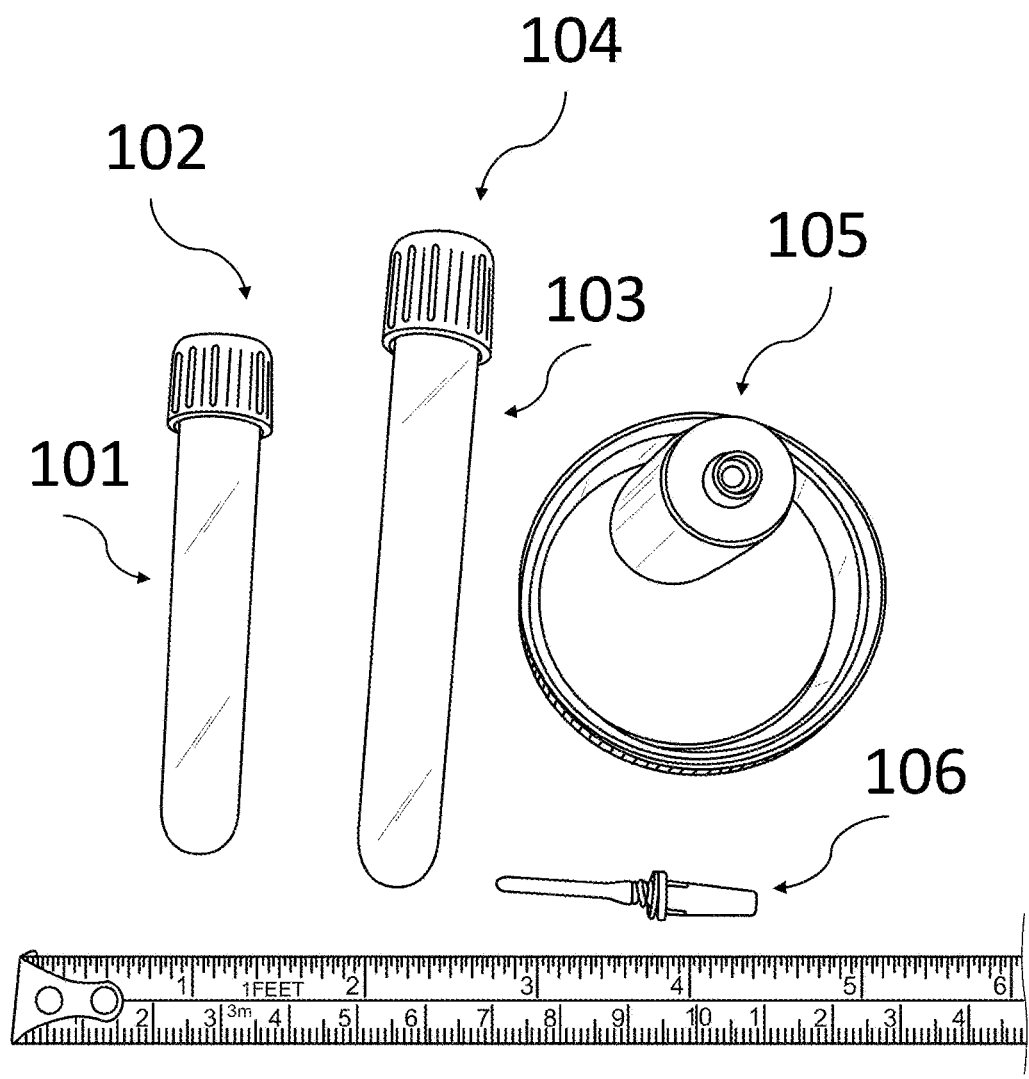
FIG. 1 (FIG. 1) illustrates representative components of a kit of the disclosure. Specifically.

All publications, patents, and patent applications mentioned in this specification are herein incorporated by reference to the same extent as if each individual publication, patent, or patent application was specifically and individually indicated to be incorporated by reference.

DETAILED DESCRIPTIONS

Urine, a biofluid produced by the kidneys, can be a source of informative biomarkers for kidney health, injury, and disease. The kidneys, collectively known as the renal system, perform the essential function of removing waste products from the blood and regulating the water fluid levels. They are essential in the urinary system, but also serve homeostatic functions such as the regulation of electrolytes, maintenance of acid-base balance, and regulation of blood pressure. They serve the body as a natural filter of the blood, and remove wastes which are diverted to the urinary bladder. In producing urine, the kidneys excrete wastes such as urea and ammonium, and they are also responsible for the reabsorption of water, glucose, and amino acids. If the right biomarker, or combination of biomarkers, is (are) identified, a urine sample can provide a suitable, non-invasive source of material for the evaluation of a solid allograft status. Urine can contain sufficient biomarkers to inform the status of kidney allografts with high sensitivity and accuracy, and it may be able to inform the status of other allografts as well.

Sarwal and colleagues investigated uses of various samples, including urine, as non-invasive sources of other informative biomarkers for the monitoring of different types of solid organ transplants (See, e.g., Sarwal WO2014/145232). Sarwal recognized that Alu elements are the most abundant transposable elements in the human genome, containing over one million copies dispersed throughout the human genome. Recognizing the abundance of ALU repeats, Sarwal created a ratio of ALU repeats in a urine sample of a transplant patient over the number of ALU repeats in a urine sample from a normal population. The ratio could be used as a proxy of injury, however, on its own it was not sufficiently informative.

Subsequent studies explored potential combination of biomarkers as proxy's for allograft injury. For instant, QSant™ utilizes a composite score of various biomarkers of distinct biochemical characteristics, i.e., proteins, metabolites, and nucleic acids. (See Yang, Sarwal, et al., A urine score for noninvasive accurate diagnosis and prediction of kidney transplant rejection. Science Translational Medicine, 18 Mar. 2020, Vol. 12, Issue 535; see also WO20180/35340). Yang et al. demonstrated that a urinary composite score of six biomarkers—an inflammation biomarker (CXCL-10, also known as IP-10); an apoptosis biomarker (e.g., clusterin); a cfDNA biomarkers; a DNA methylation biomarker; a creatinine biomarker; and total protein—enables diagnosis of Acute Rejection (AR), with a receiver-operator characteristic curve area under the curve of 0.99 and an accuracy of 96%. Notably, QSant™ predicts acute rejection before a rise in a stand-alone serum creatinine test, enabling earlier detection of rejection than currently possible by current standard of care tests. Sarwal considered potential ways of stabilizing the samples, but it failed to conjure a combination of reagents that could stabilize a urine sample for any longer than 72 hours. See, e.g., Sarwal WO20180/35340). This is important because analyte instability in urine precludes the recipients of an allograft from providing a urine void while in the comfort of their own homes that is sufficiently stable, for example, to be used in the analysis described by Yang, Sarwal, et all. Id.

The traditional method of midstream urine collection is for the healthcare professional to give the patient some sort of pot in which to collect their urine; this could be a universal container, a small tub, or a cup which the collecting physician may or may not store in different containers. In the laboratory, the specimen is typically decanted again, into a secondary primary tube. One specimen can therefore be decanted and handled two or three times before it reaches the laboratory, and there is no guarantee it has not been stored properly or under conditions that preserve the urine sample for further analysis. Further, it is extremely difficult to control the amount of sample being collected by a patient in a container. Further, patients are not positioned to collect precise amounts of samples and combine such precise amounts with any other chemical reagent.

The present disclosure provides kits for the stabilization of a plurality of markers in a urine sample from a subject that can stabilize the biomarkers in the urine sample for a suitable period-of-time such that the sample can be collected at a subject's home and analyzed days later at a laboratory. Such kits are created, designed, and configured to collect defined amounts of urine samples in containers such that these amounts are mixed with preservatives pre-packaged in the container in suitable ratios for preserving the urine sample. Preferably, such kits can stabilize a urine sample for at least 5 days at room temperature. Preferably, such kits can stabilize a urine sample in a range of temperatures, including temperatures up to 86° F., to support an analysis of a sample that has been exposed to varying temperatures while being routed to a laboratory.

Figure 2:
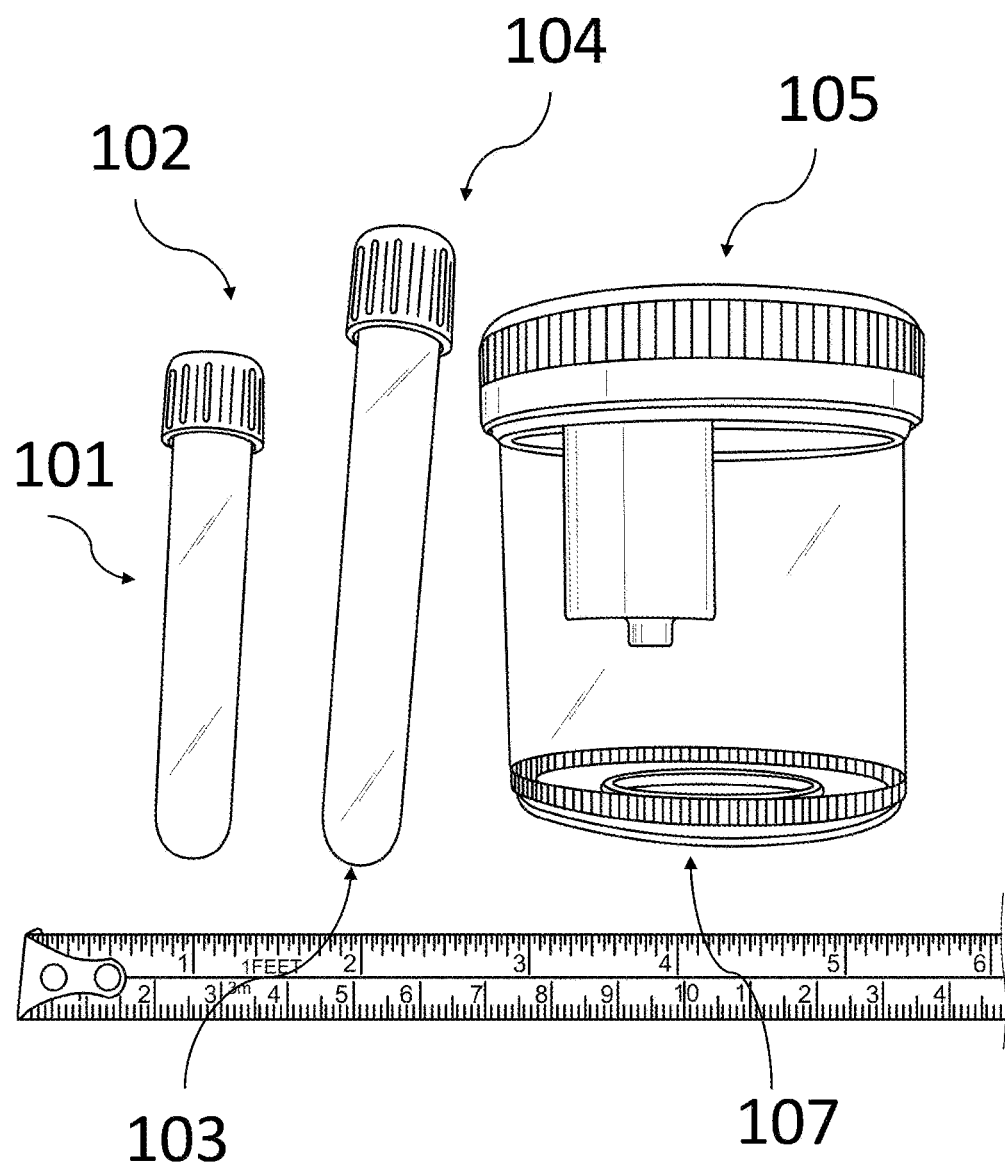
FIG. 2 (FIG. 2) illustrates representative components of a kit of the disclosure. Specifically.
Figure 3:
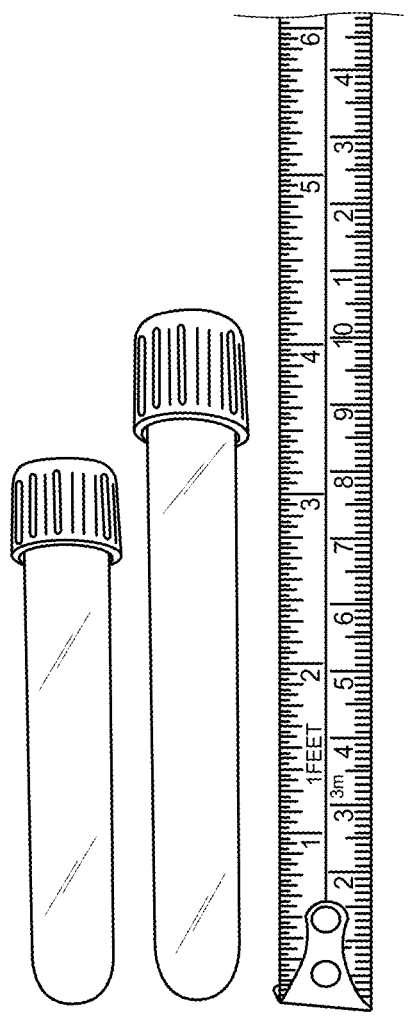
FIG. 3 (FIG. 3) illustrates representative dimensions of urine sample collection tubes used with a kit of the disclosure.
Figure 4:
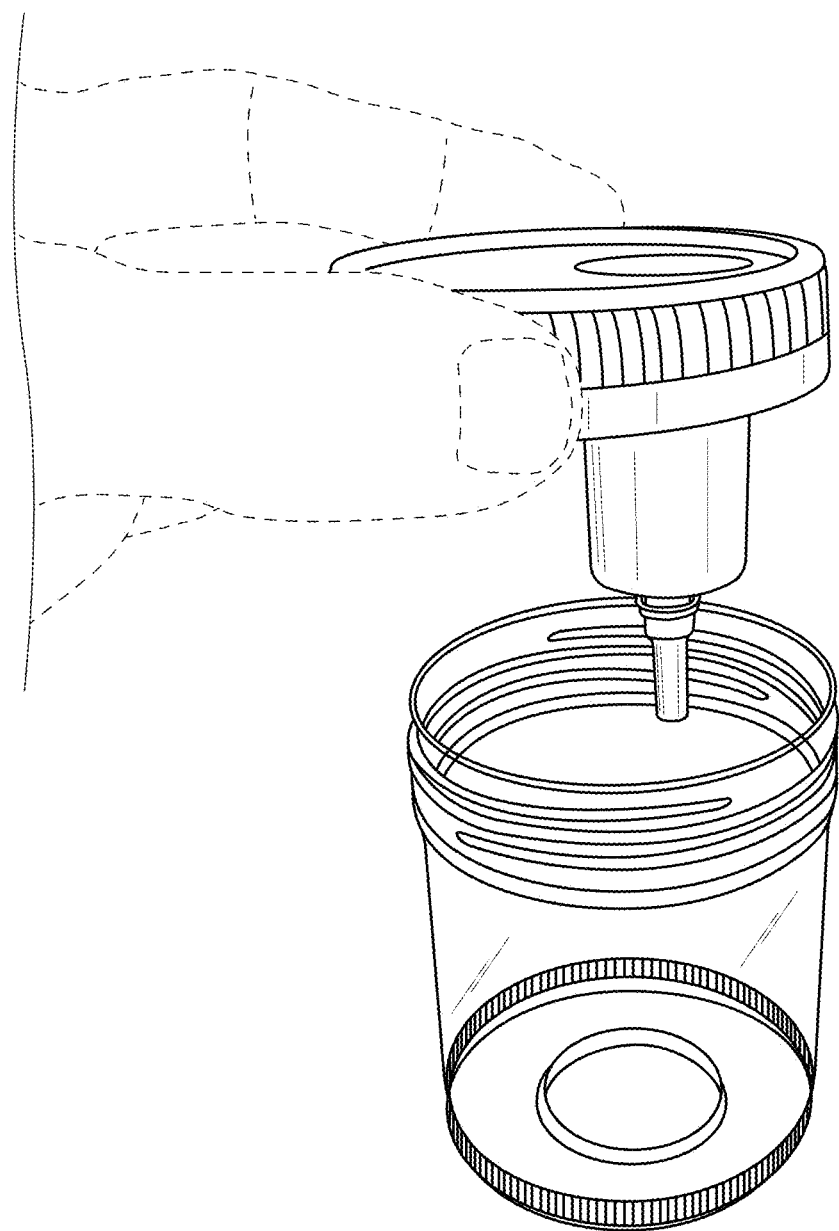
FIG. 4 (FIG. 4) illustrates a subject opening a vacutainer, which can be done prior to the subject providing a urine sample into the vacutainer.
Figure 5:
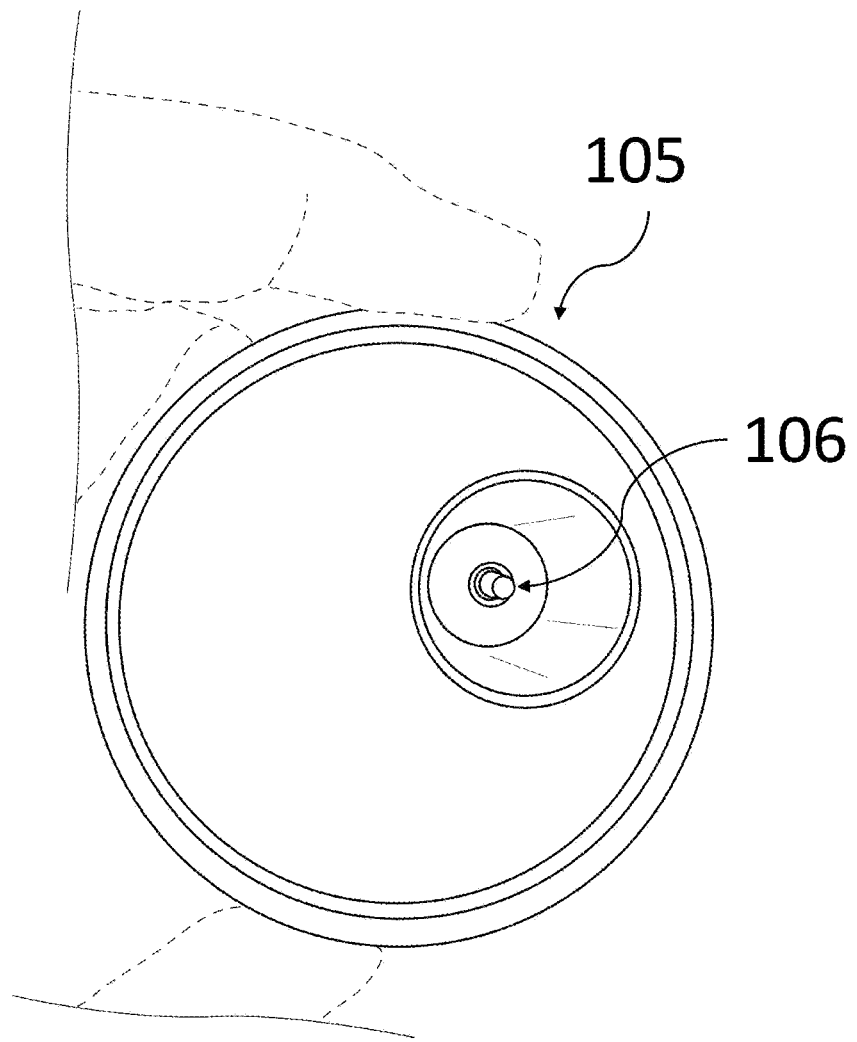
FIG. 5 (FIG. 5) illustrates an inner protrusion of the lid of the vacutainer top functionally connected to a piercing hollow channel 106. Each one of the collection tubes tops illustrated in FIG. 3 can be pressed against the piercing hollow channel for urine sample collection.
Figure 6:
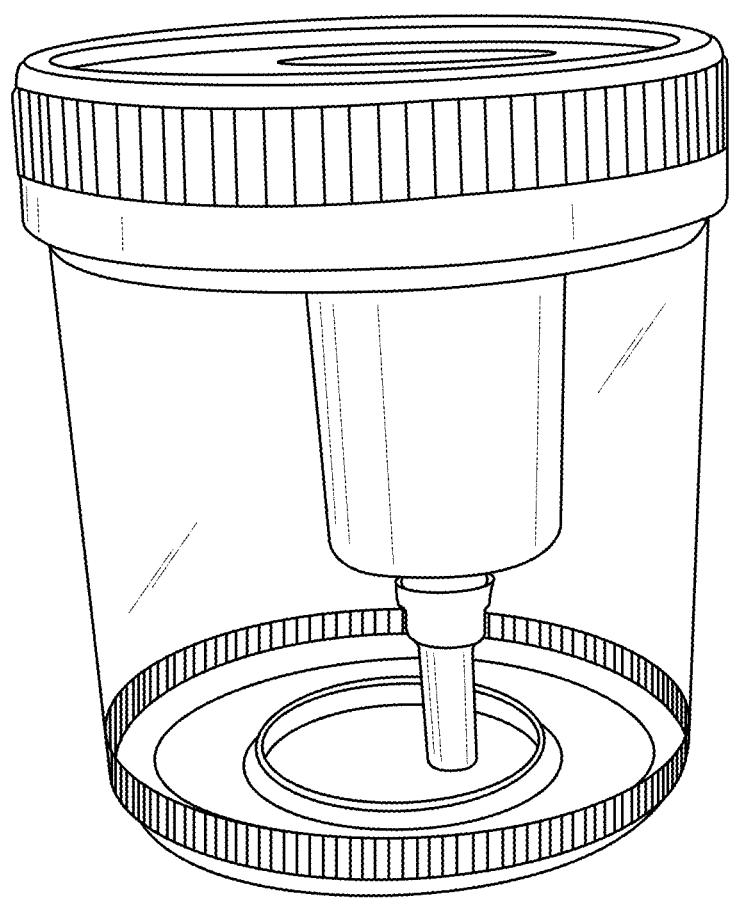
FIG. 6 (FIG. 6) illustrates an assembled vacutainer of the disclosure.
Figure 8:
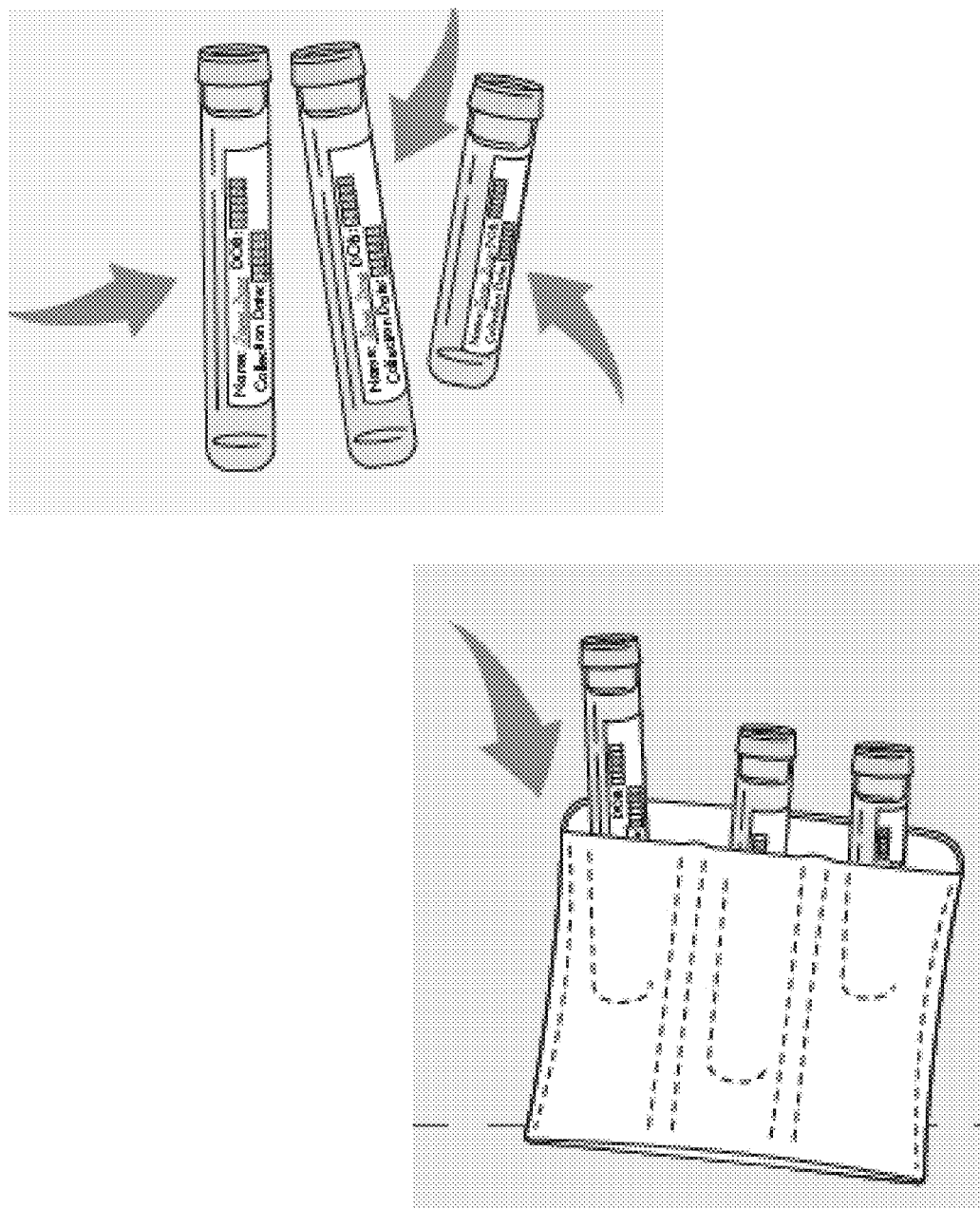
FIG. 8 (FIG. 8) illustrates the labeling of individual tubes and insertion of each tube into a sleeve.
Figure 9:
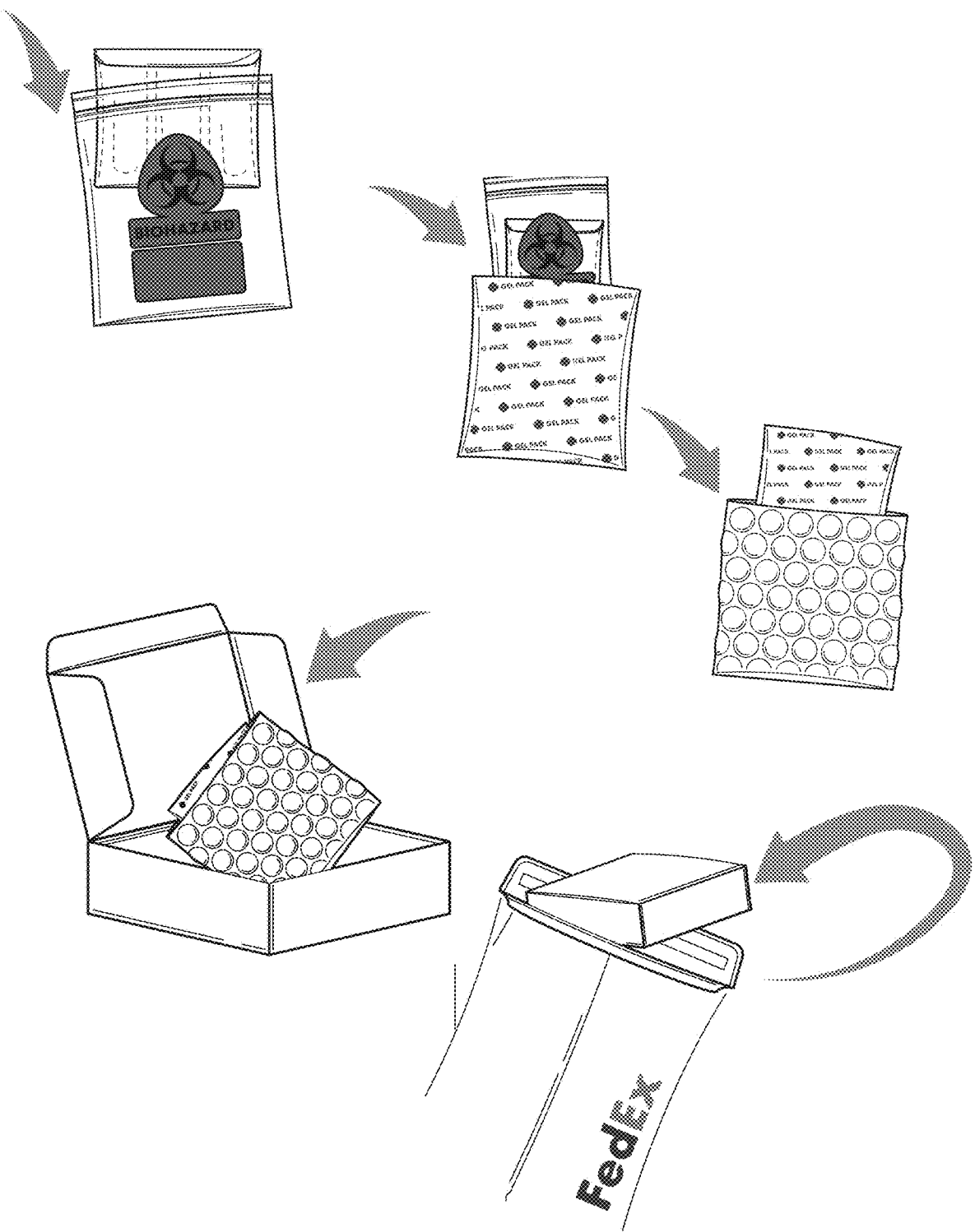
FIG. 9 (FIG. 9) illustrates the shipping process of samples with an exemplary kit of the disclosure.
Figure 10:
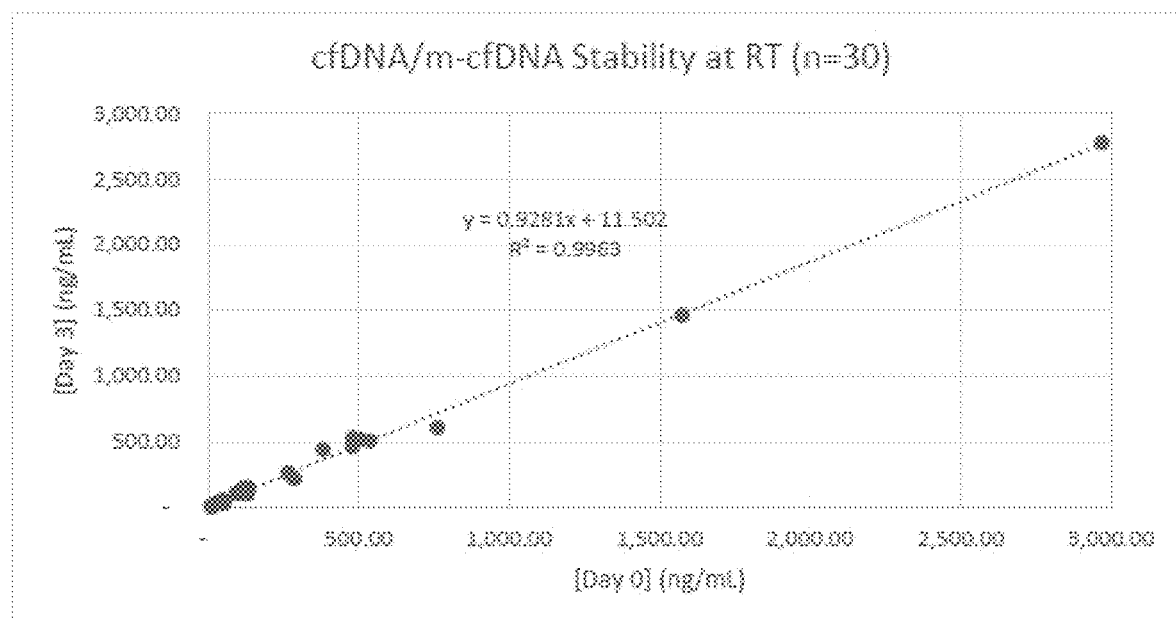
FIG. 10 (FIG. 10) illustrates cfDNA/m-cfDNA Stability at RT (n=30).
Figure 11:
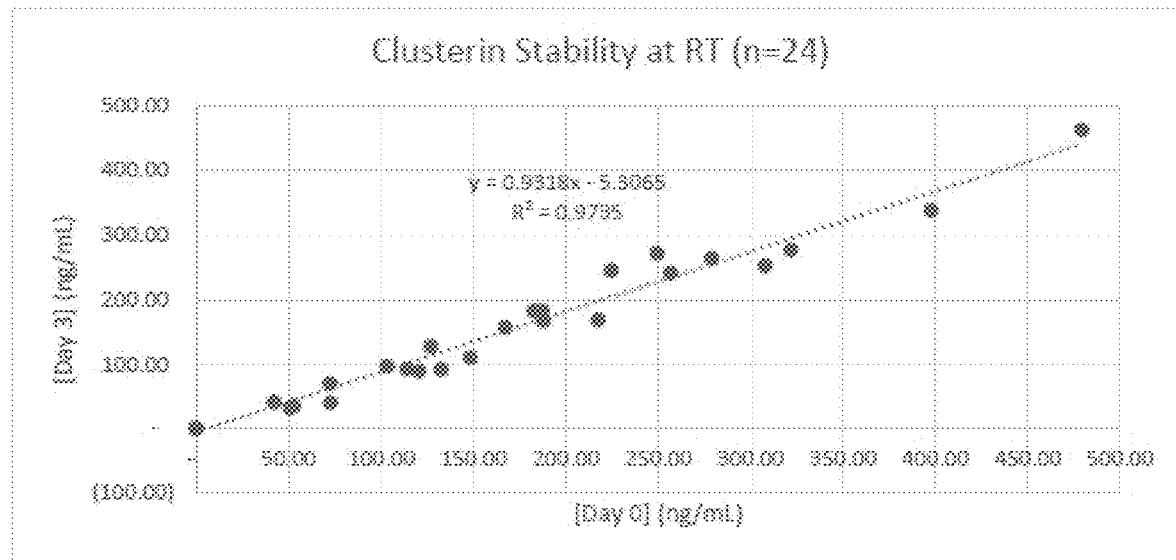
FIG. 11 (FIG. 11) illustrates Clusterin Stability at RT (n=24).
Figure 12:
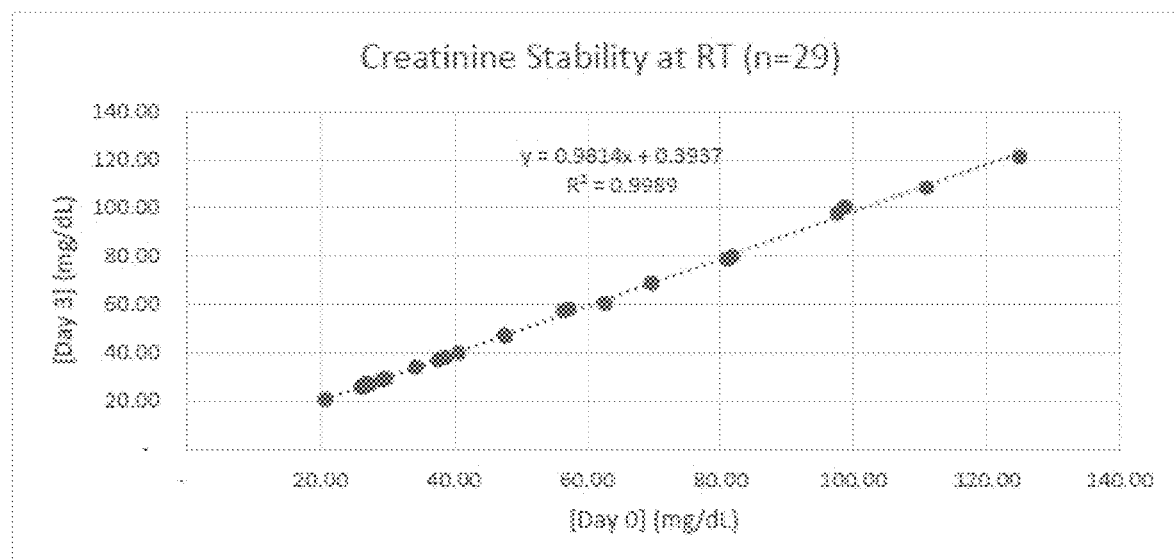
FIG. 12 (FIG. 12) illustrates Creatinine Stability at RT (n=29).
Figure 13:
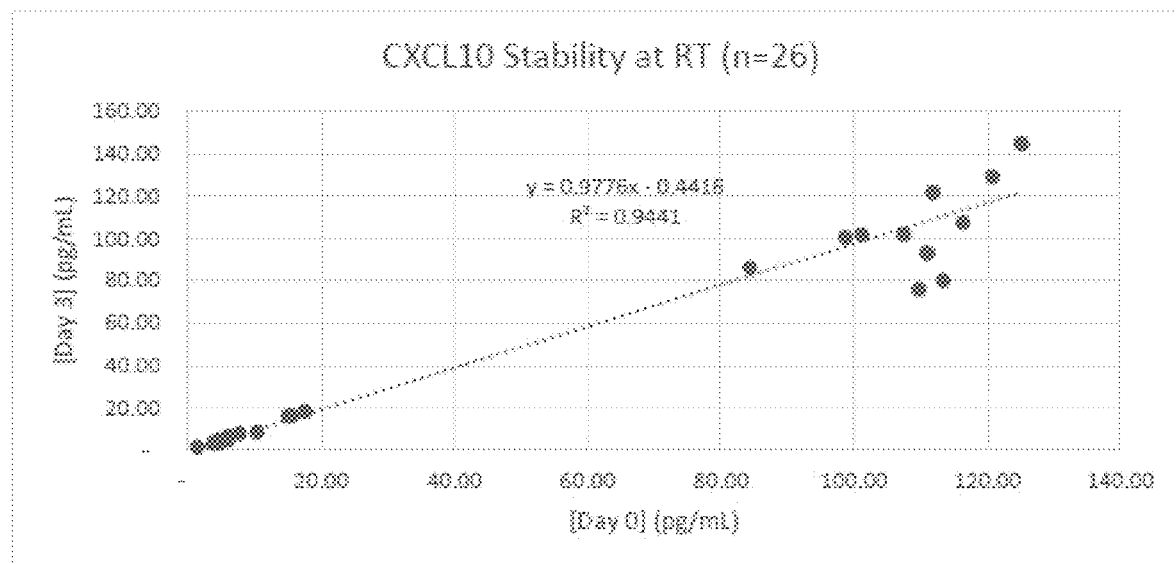
FIG. 13 (FIG. 13) illustrates CXCL10 Stability at RT (n=26).
Figure 14:
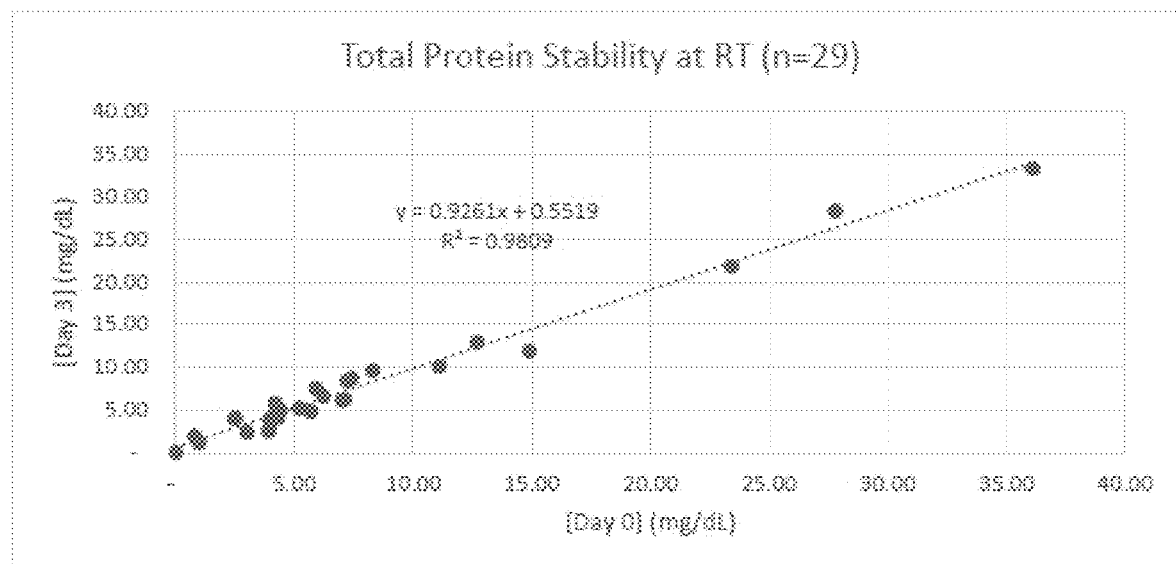
FIG. 14 (FIG. 14) illustrates Total Protein Stability at RT (n=29).

In some cases, provided herein are vacutainer kits for both collecting and stabilizing a sample for at least 5 days at room temperature and above. In preferred embodiments, a subject receives in the mail, by a postal courier, a urine testing kit comprising a vacutainer and one or more collection tubes (FIGS. 1-3) pre-packaged with liquid forms, powder forms, or gel forms of a stabilizing solution. Alternatively, the pre-packed solution can be also be sprayed onto the sides of the collection tube. In most preferred embodiments, the vacutainer cup having a screw top lid (FIG. 4) having an inner protrusion functionally connected to a piercing hollow channel (FIG. 5). Once the urine specimen is introduced into the vacutainer, the vacutainer's lid is closed thus forming a seal (FIG. 6). Each one of the individual urine sample collection tubes is pressed against the piercing channel of the vacutainer which releases an amount of urine inside the collection tubes. The collection tubes may be "inverted 5-10 times" until the urine sample is mixed with the pre-packaged stabilizer solution inside the collection tube.

Stabilizing Urine Biomarkers in Collection Tubes of the Disclosed Kits cfDNA and Total Protein Sample Collection Tubes In one aspect, the instant disclosure provides a kit and methods for collecting a urine sample comprising a cell-free DNA (cfDNA) and keeping it stable. Cell-free DNA naturally occurs in biofluids such as blood and has been largely attributed to apoptotic and necrotic processes. While the presence of cfDNA in blood was discovered in 1948, its implications in clinical medicine were not realized for more than two decades. Much less is known about the abundance and the utility of cfDNA from urine samples.

Since that time, a cumulative body of research has identified cfDNA and m-cfDNA as both a prognostic and diagnostic indicator for multiple pathogenic conditions; i.e., allograft rejection, kidney injury, and various cancers, See, e.g., Sarwal WO20180/35340). As such, accurate detection of cfDNA and m-cfDNA in human biological specimens may provide a non-invasive avenue that allows assessment, screening, and disease classification and monitoring, if the outstanding challenges of keeping the sample stable are successfully overcome. The detection of cfDNA, however, is particularly challenging for the following reasons: (1) sample processing after collection can induce cell lysis, which often leads to aberrant increases in the amount of circulating cfDNA, and (2) the relatively low level of cfDNA underscores the potential risks of generating false negative results due to the loss of scarce target cfDNA sequences-due to sample instability or inappropriate sample processing.

Due to the low abundance of the cfDNA biomarkers in any sample, and especially due to its particularly low abundance in urine samples, it is recommended that genomic DNA (gDNA) background levels be minimized to provide accurate measurements of cfDNA levels (the average circulating concentration of cfDNA for a healthy individual is 30 ng/ml, the cfDNA is generally double stranded, and approximately 0.18-21 kilobases in size (See Wagner, J. "Free DNA new potential analyte in clinical laboratory diagnostics?" Biochem Med (Zagreb) 22(1): 24-38)). It is further beneficial that the structural integrity of the cfDNA be maintained due to the minimal amounts available for analysis. It is therefore necessary to address several pre-analytical issues that arise during the time between urine collection and subsequent DNA isolation. These issues include the ability to combine suitable amounts of urine with suitable ratios of preservatives, delays in urine processing, urine storage temperature, and agitation of the sample during transport and shipment of urine. Such conditions may alter urinary DNA levels by causing gDNA release from lysed bladder and uroepithelial cells and obfuscate true cfDNA. As a result, it is important to consider the type of urine collection device and post-collection conditions while working with cfDNA samples.

The disclosure provided herein, provides strategies for combining suitable amounts of urine with an upper limit of volume defined by the capacity of the container which overcomes challenges in having a subject provide a suitable amount of urine at home and combine it with a suitable amount of preservative (See FIGS. 1-8). In many aspects, the kits and vacutainer kits provided herein require a minimum amount of preservative to maintain the biomarker in a state that is suitable for analysis. In many instances, an excess amount of preservative as provided in a vacutainer of the disclosure does not affect the ability of a biomarker to be further analyzed, but a minimum amount of preservative is required. Usefully, the format of the kit, namely vacutainers pre-packed with a suitable concentration of a preservative for a set of biomarkers, allow a subject to collect the urine sample at home, without the need of either a venipuncture or more challenging manipulation of a suitable manipulation of urine to preservative ratios in open containers by the subjects.

In preferred instances, the collection tubes that stabilize the cfDNA also stabilize an amount of the total protein in the urine sample. The measurement of urine total protein is central to the diagnosis and management of subjects with kidney disease/injury. For instance, proteinuria is a strong predictor of adverse cardiovascular and kidney events, and an accurate assessment of proteinuria is important for the evaluation and management of CKD. Proteinuria has been associated with transplant loss and mortality in kidney transplant recipients. Both spot samples (albumin-creatinine ratio (ACR) and protein-creatinine ratio (PCR) and 24-hour collections (albumin excretion rate (AER) and protein excretion rate (PER)) have been used to quantify protein excretion, but which measurement is a better predictor of outcomes in kidney transplantation remains uncertain. The present disclosure provides a kit and methods for collecting urine samples and shipping them to a laboratory that stabilizes both a cfDNA and an amount of the total protein in a sample for at least 5 days at room temperature.

For blood and serum samples, the art discloses the addition of anticoagulants such as heparin, sodium fluoride (NaF), and citrate are generally added to collection tubes to prevent clotting of whole blood cells, which is thought to reduce DNA release from the leukocyte cell population. Also, the optimization of centrifugation conditions is required to prevent lysis but adequately separate intact cells from cell-free plasma. Because healthy urine samples generally have scant cellularity the disclosure provides better and distinct stabilizing solutions that more effectively preserve the analyte, as opposed to merely preserving cell death. In some aspects, the disclosure provides a kit that has a urine collection tube pre-packaged with a formaldehyde donor. Typical formaldehyde donors used in urine collection tubes of the disclosure include DMDM hydantoin (DMDMH), imadazolidinyl urea, diazlidinyl urea, sodium hydroxyl and methyl glycinate. In many instances, an excess amount of formaldehyde as provided in a vacutainer of the disclosure does not affect the ability of the particular biomarker to be further analyzed, but a minimum amount of preservative is required. Pre-packaging in the vacutainers of the disclosure provides a suitable amount of preservative for combining with a volume of urine that is in the range of 1 mL to 20 mLs; in the range of 1 mL to 15 mLs; in the range of 1 mL to 10 mLs; in the range of 1 mL to 5 mLs; or another suitable amounts within those ranges.

Alternatively the formaldehyde donor could be added to the collection tube in powder format. In these instances, the concentration of the powder in the rube would be calculated accordingly to provide a dilution ratio of about 1:5. The urine sample collection tube can be a 5 milliliter collection tube, a 10 milliliter collection tube, a 12 milliliter collection tube, or another suitable size and the concentrated amount of formaldehyde can be adjusted accordingly to provide a dilution ratio of about 1:5.

Addition of a formaldehyde donor may prevent subsequent amplification of some cfDNA genes, notheless in preferred instances the subsequent detection of cfDNA in the urine samples does not require amplification. In such instances, presence of cfDNA in a sample can be inferred from the presence of an Alu repeat—or another suitable region—in the cfDNA without amplification. Alu elements belong to a primate specific class of retroelements termed SINEs (short interspersed elements). There are over one million Alu elements interspersed throughout the human genome, and it is estimated that about 10.7% of the human genome consists of Alu sequences. However, less than 0.5% are polymorphic (i.e., occurring in more than one form or morph). The typical structure of an Alu element is 5'-Part A—ASTACA6-Part B—PolyA Tail-3', where Part A and Part B (also known as "left arm" and "right arm") are similar nucleotide sequences. Alu repeats are similarly abundantly present in cfDNA. Thus, detection of Alu sequences from short cfDNA fragments can be used as a biomarker for detection of cfDNA, even if the sample has been stabilized with a solution that otherwise, for example, includes a formaldehyde donor.

A urine collection tube of the disclosure may be pre-packed with anywhere from: 25 g/L-800 g/L of a formaldehyde donor, 50 g/L-800 g/L of a formaldehyde donor, 75 g/L-800 g/L of a formaldehyde donor, 100 g/L-800 g/L of a formaldehyde donor, 125 g/L-800 g/L of a formaldehyde donor, 150 g/L-800 g/L of a formaldehyde donor, 175 g/L-800 g/L of a formaldehyde donor, 200 g/L-800 g/L of a formaldehyde donor, 225 g/L-800 g/L of a formaldehyde donor, 250 g/L-800 g/L of a formaldehyde donor, 275 g/L-800 g/L of a formaldehyde donor, 300 g/L-800 g/L of a formaldehyde donor, 325 g/L-800 g/L of a formaldehyde donor, 350 g/L-800 g/L of a formaldehyde donor, 375 g/L-800 g/L of a formaldehyde donor, 400 g/L-800 g/L of a formaldehyde donor, 425 g/L-800 g/L of a formaldehyde donor, 450 g/L-800 g/L of a formaldehyde donor, 475 g/L-800 g/L of a formaldehyde donor, 500 g/L-800 g/L of a formaldehyde donor, 525 g/L-800 g/L of a formaldehyde donor, 550 g/L-800 g/L of a formaldehyde donor, 575 g/L-800 g/L of a formaldehyde donor, 600 g/L-800 g/L of a formaldehyde donor, 625 g/L-800 g/L of a formaldehyde donor, 650 g/L-800 g/L of a formaldehyde donor, 675 g/L-800 g/L of a formaldehyde donor, 700 g/L-800 g/L of a formaldehyde donor, 725 g/L-800 g/L of a formaldehyde donor, 750 g/L-800 g/L of a formaldehyde donor, 775 g/L-800 g/L of a formaldehyde donor, 50 g/L-700 g/L of a formaldehyde donor, 75 g/L-700 g/L of a formaldehyde donor, 100 g/L-700 g/L of a formaldehyde donor, 125 g/L-700 g/L of a formaldehyde donor, 150 g/L-700 g/L of a formaldehyde donor, 175 g/L-700 g/L of a formaldehyde donor, 200 g/L-700 g/L of a formaldehyde donor, 225 g/L-700 g/L of a formaldehyde donor, 250 g/L-700 g/L of a formaldehyde donor, 275 g/L-700 g/L of a formaldehyde donor, 300 g/L-700 g/L of a formaldehyde donor, 325 g/L-700 g/L of a formaldehyde donor, 350 g/L-700 g/L of a formaldehyde donor, 375 g/L-700 g/L of a formaldehyde donor, 400 g/L-700 g/L of a formaldehyde donor, 425 g/L-700 g/L of a formaldehyde donor, 450 g/L-700 g/L of a formaldehyde donor, 475 g/L-700 g/L of a formaldehyde donor, 500 g/L-700 g/L of a formaldehyde donor, 525 g/L-700 g/L of a formaldehyde donor, 550 g/L-700 g/L of a formaldehyde donor, 575 g/L-700 g/L of a formaldehyde donor, 600 g/L-700 g/L of a formaldehyde donor, 625 g/L-700 g/L of a formaldehyde donor, 650 g/L-700 g/L of a formaldehyde donor, 675 g/L-700 g/L of a formaldehyde donor, 50 g/L-600 g/L of a formaldehyde donor, 75 g/L-600 g/L of a formaldehyde donor, 100 g/L-600 g/L of a formaldehyde donor, 125 g/L-600 g/L of a formaldehyde donor, 150 g/L-600 g/L of a formaldehyde donor, 175 g/L-600 g/L of a formaldehyde donor, 200 g/L-600 g/L of a formaldehyde donor, 225 g/L-600 g/L of a formaldehyde donor, 250 g/L-600 g/L of a formaldehyde donor, 275 g/L-600 g/L of a formaldehyde donor, 300 g/L-600 g/L of a formaldehyde donor, 325 g/L-600 g/L of a formaldehyde donor, 350 g/L-600 g/L of a formaldehyde donor, 375 g/L-600 g/L of a formaldehyde donor, 400 g/L-600 g/L of a formaldehyde donor, 425 g/L-600 g/L of a formaldehyde donor, 450 g/L-600 g/L of a formaldehyde donor, 475 g/L-600 g/L of a formaldehyde donor, 500 g/L-600 g/L of a formaldehyde donor, 525 g/L-600 g/L of a formaldehyde donor, 550 g/L-600 g/L of a formaldehyde donor, 575 g/L-600 g/L of a formaldehyde donor, 50 g/L-500 g/L of a formaldehyde donor, 75 g/L-500 g/L of a formaldehyde donor, 100 g/L-500 g/L of a formaldehyde donor, 125 g/L-500 g/L of a formaldehyde donor, 150 g/L-500 g/L of a formaldehyde donor, 175 g/L-500 g/L of a formaldehyde donor, 200 g/L-500 g/L of a formaldehyde donor, 225 g/L-500 g/L of a formaldehyde donor, 250 g/L-500 g/L of a formaldehyde donor, 275 g/L-500 g/L of a formaldehyde donor, 300 g/L-500 g/L of a formaldehyde donor, 325 g/L-500 g/L of a formaldehyde donor, 350 g/L-500 g/L of a formaldehyde donor, 375 g/L-500 g/L of a formaldehyde donor, 400 g/L-500 g/L of a formaldehyde donor, 425 g/L-500 g/L of a formaldehyde donor, 450 g/L-500 g/L of a formaldehyde donor, 475 g/L-500 g/L of a formaldehyde donor, 50 g/L-400 g/L of a formaldehyde donor, 75 g/L-400 g/L of a formaldehyde donor, 100 g/L-400 g/L of a formaldehyde donor, 125 g/L-400 g/L of a formaldehyde donor, 150 g/L-400 g/L of a formaldehyde donor, 175 g/L-400 g/L of a formaldehyde donor, 200 g/L-400 g/L of a formaldehyde donor, 225 g/L-400 g/L of a formaldehyde donor, 250 g/L-400 g/L of a formaldehyde donor, 275 g/L-400 g/L of a formaldehyde donor, 300 g/L-400 g/L of a formaldehyde donor, 325 g/L-400 g/L of a formaldehyde donor, 350 g/L-400 g/L of a formaldehyde donor, 375 g/L-400 g/L of a formaldehyde donor, 50 g/L-300 g/L of a formaldehyde donor, 75 g/L-300 g/L of a formaldehyde donor, 100 g/L-300 g/L of a formaldehyde donor, 125 g/L-300 g/L of a formaldehyde donor, 150 g/L-300 g/L of a formaldehyde donor, 175 g/L-300 g/L of a formaldehyde donor, 200 g/L-300 g/L of a formaldehyde donor, 225 g/L-300 g/L of a formaldehyde donor, 250 g/L-300 g/L of a formaldehyde donor. In preferred instances, each collection tube in the kit is pre-packed with wherein the volume of the pre-packaged solution ranges from 0.5 milliliters to 4 milliliters. Such amounts provide for a concentrated amount of formaldehyde that is generally diluted about 5-fold by the addition of the urine sample.

The urine collection sample of the disclosure may also be pre-packed with a quenching agent to minimize protein-protein crosslinking that may occur due to formaldehyde addition. The quenching solution may be any agent known to quench excess formaldehyde including, but not limited to glycine. In many instances, an excess amount of a quenching solution as provided in a vacutainer of the disclosure does not affect the ability of the particular biomarker to be further analyzed—it is largely used to quench the excess of formaldehyde in a sample—but a minimum amount of preservative is required. Pre-packaging in the vacutainers of the disclosure provides a suitable amount of a quenching agent for combining with a volume of urine that is in the range of 1 mL to 20 mLs; in the range of 1 mL to 15 mLs; in the range of 1 mL to 10 mLs; in the range of 1 mL to 5 mLs; or another suitable amounts within those ranges. A urine collection tube of the disclosure may be pre-packed with anywhere from: 2.5 g/L-80 g/L of a quenching agent, 5 g/L-80 g/L of a quenching agent, 7.5 g/L-80 g/L of a quenching agent, 10 g/L-80 g/L of a quenching agent, 12.5 g/L-80 g/L of a quenching agent, 15 g/L-80 g/L of a quenching agent, 1.75 g/L-80 g/L of a quenching agent, 2 g/L-80 g/L of a quenching agent, 2.25 g/L-80 g/L of a quenching agent, 2.5 g/L-80 g/L of a quenching agent, 2.75 g/L-80 g/L of a quenching agent, 3 g/L-80 g/L of a quenching agent, 3.25 g/L-80 g/L of a quenching agent, 3.5 g/L-80 g/L of a quenching agent, 3.75 g/L-80 g/L of a quenching agent, 4 g/L-80 g/L of a quenching agent, 4.25 g/L-80 g/L of a quenching agent, 4.5 g/L-80 g/L of a quenching agent, 4.75 g/L-80 g/L of a quenching agent, 5 g/L-80 g/L of a quenching agent, 5.25 g/L-80 g/L of a quenching agent, 5.5 g/L-80 g/L of a quenching agent, 5.75 g/L-80 g/L of a quenching agent, 6 g/L-80 g/L of a quenching agent, 6.25 g/L-80 g/L of a quenching agent, 6.5 g/L-80 g/L of a quenching agent, 6.75 g/L-80 g/L of a quenching agent, 7 g/L-80 g/L of a quenching agent, 7.25 g/L-80 g/L of a quenching agent, 7.5 g/L-80 g/L of a quenching agent, 8 g/L-80 g/L of a quenching agent, 8.25 g/L-80 g/L of a quenching agent, 8.5 g/L-80 g/L of a quenching agent, 8.75 g/L-80 g/L of a quenching agent, 9 g/L-80 g/L of a quenching agent, 9.25 g/L-80 g/L of a quenching agent, 9.5 g/L-80 g/L of a quenching agent, 9.75 g/L-80 g/L of a quenching agent, 10 g/L-80 g/L of a quenching agent, 10.25 g/L-80 g/L of a quenching agent, 10.5 g/L-80 g/L of a quenching agent, 10.75 g/L-80 g/L of a quenching agent, 11 g/L-80 g/L of a quenching agent, 11.25 g/L-80 g/L of a quenching agent, 11.5 g/L-80 g/L of a quenching agent, 11.75 g/L-80 g/L of a quenching agent, 12 g/L-80 g/L of a quenching agent, 12.25 g/L-80 g/L of a quenching agent, 12.5 g/L-80 g/L of a quenching agent, 12.75 g/L-80 g/L of a quenching agent, 13 g/L-80 g/L of a quenching agent, 13.25 g/L-80 g/L of a quenching agent, 13.5 g/L-80 g/L of a quenching agent, 13.75 g/L-80 g/L of a quenching agent, 14 g/L-80 g/L of a quenching agent, 14.25 g/L-80 g/L of a quenching agent, 14.5 g/L-80 g/L of a quenching agent, 14.75 g/L-80 g/L of a quenching agent, 15 g/L-80 g/L of a quenching agent, 2.5 g/L-70 g/L of a quenching agent, 5 g/L-70 g/L of a quenching agent, 7.5 g/L-70 g/L of a quenching agent, 10 g/L-70 g/L of a quenching agent, 12.5 g/L-70 g/L of a quenching agent, 15 g/L-70 g/L of a quenching agent, 1.75 g/L-70 g/L of a quenching agent, 2 g/L-70 g/L of a quenching agent, 2.25 g/L-70 g/L of a quenching agent, 2.5 g/L-70 g/L of a quenching agent, 2.75 g/L-70 g/L of a quenching agent, 3 g/L-70 g/L of a quenching agent, 3.25 g/L-70 g/L of a quenching agent, 3.5 g/L-70 g/L of a quenching agent, 3.75 g/L-70 g/L of a quenching agent, 4 g/L-70 g/L of a quenching agent, 4.25 g/L-70 g/L of a quenching agent, 4.5 g/L-70 g/L of a quenching agent, 4.75 g/L-70 g/L of a quenching agent, 5 g/L-70 g/L of a quenching agent, 5.25 g/L-70 g/L of a quenching agent, 5.5 g/L-70 g/L of a quenching agent, 5.75 g/L-70 g/L of a quenching agent, 6 g/L-70 g/L of a quenching agent, 6.25 g/L-70 g/L of a quenching agent, 6.5 g/L-70 g/L of a quenching agent, 6.75 g/L-70 g/L of a quenching agent, 7 g/L-70 g/L of a quenching agent, 7.25 g/L-70 g/L of a quenching agent, 7.5 g/L-70 g/L of a quenching agent, 8 g/L-70 g/L of a quenching agent, 8.25 g/L-70 g/L of a quenching agent, 8.5 g/L-70 g/L of a quenching agent, 8.75 g/L-70 g/L of a quenching agent, 9 g/L-70 g/L of a quenching agent, 9.25 g/L-70 g/L of a quenching agent, 9.5 g/L-70 g/L of a quenching agent, 9.75 g/L-70 g/L of a quenching agent, 10 g/L-70 g/L of a quenching agent, 10.25 g/L-70 g/L of a quenching agent, 10.5 g/L-70 g/L of a quenching agent, 10.75 g/L-70 g/L of a quenching agent, 11 g/L-70 g/L of a quenching agent, 11.25 g/L-70 g/L of a quenching agent, 11.5 g/L-70 g/L of a quenching agent, 11.75 g/L-70 g/L of a quenching agent, 12 g/L-70 g/L of a quenching agent, 12.25 g/L-70 g/L of a quenching agent, 12.5 g/L-70 g/L of a quenching agent, 12.75 g/L-70 g/L of a quenching agent, 13 g/L-70 g/L of a quenching agent, 13.25 g/L-70 g/L of a quenching agent, 13.5 g/L-70 g/L of a quenching agent, 13.75 g/L-70 g/L of a quenching agent, 14 g/L-70 g/L of a quenching agent, 14.25 g/L-70 g/L of a quenching agent, 14.5 g/L-70 g/L of a quenching agent, 14.75 g/L-70 g/L of a quenching agent, 15 g/L-70 g/L of a quenching agent, 2.5 g/L-60 g/L of a quenching agent, 5 g/L-60 g/L of a quenching agent, 7.5 g/L-60 g/L of a quenching agent, 10 g/L-60 g/L of a quenching agent, 12.5 g/L-60 g/L of a quenching agent, 15 g/L-60 g/L of a quenching agent, 1.75 g/L-60 g/L of a quenching agent, 2 g/L-60 g/L of a quenching agent, 2.25 g/L-60 g/L of a quenching agent, 2.5 g/L-60 g/L of a quenching agent, 2.75 g/L-60 g/L of a quenching agent, 3 g/L-60 g/L of a quenching agent, 3.25 g/L-60 g/L of a quenching agent, 3.5 g/L-60 g/L of a quenching agent, 3.75 g/L-60 g/L of a quenching agent, 4 g/L-60 g/L of a quenching agent, 4.25 g/L-60 g/L of a quenching agent, 4.5 g/L-60 g/L of a quenching agent, 4.75 g/L-60 g/L of a quenching agent, 5 g/L-60 g/L of a quenching agent, 5.25 g/L-60 g/L of a quenching agent, 5.5 g/L-60 g/L of a quenching agent, 5.75 g/L-60 g/L of a quenching agent, 6 g/L-60 g/L of a quenching agent, 6.25 g/L-60 g/L of a quenching agent, 6.5 g/L-60 g/L of a quenching agent, 6.75 g/L-60 g/L of a quenching agent, 7 g/L-60 g/L of a quenching agent, 7.25 g/L-60 g/L of a quenching agent, 7.5 g/L-60 g/L of a quenching agent, 8 g/L-60 g/L of a quenching agent, 8.25 g/L-60 g/L of a quenching agent, 8.5 g/L-60 g/L of a quenching agent, 8.75 g/L-60 g/L of a quenching agent, 9 g/L-60 g/L of a quenching agent, 9.25 g/L-60 g/L of a quenching agent, 9.5 g/L-60 g/L of a quenching agent, 9.75 g/L-60 g/L of a quenching agent, 10 g/L-60 g/L of a quenching agent, 10.25 g/L-60 g/L of a quenching agent, 10.5 g/L-60 g/L of a quenching agent, 10.75 g/L-60 g/L of a quenching agent, 11 g/L-60 g/L of a quenching agent, 11.25 g/L-60 g/L of a quenching agent, 11.5 g/L-60 g/L of a quenching agent, 11.75 g/L-60 g/L of a quenching agent, 12 g/L-60 g/L of a quenching agent, 12.25 g/L-60 g/L of a quenching agent, 12.5 g/L-60 g/L of a quenching agent, 12.75 g/L-60 g/L of a quenching agent, 13 g/L-60 g/L of a quenching agent, 13.25 g/L-60 g/L of a quenching agent, 13.5 g/L-60 g/L of a quenching agent, 13.75 g/L-60 g/L of a quenching agent, 14 g/L-60 g/L of a quenching agent, 14.25 g/L-60 g/L of a quenching agent, 14.5 g/L-60 g/L of a quenching agent, 14.75 g/L-60 g/L of a quenching agent, 15 g/L-60 g/L of a quenching agent, 2.5 g/L-50 g/L of a quenching agent, 5 g/L-50 g/L of a quenching agent, 7.5 g/L-50 g/L of a quenching agent, 10 g/L-50 g/L of a quenching agent, 12.5 g/L-50 g/L of a quenching agent, 15 g/L-50 g/L of a quenching agent, 1.75 g/L-50 g/L of a quenching agent, 2 g/L-50 g/L of a quenching agent, 2.25 g/L-50 g/L of a quenching agent, 2.5 g/L-50 g/L of a quenching agent, 2.75 g/L-50 g/L of a quenching agent, 3 g/L-50 g/L of a quenching agent, 3.25 g/L-50 g/L of a quenching agent, 3.5 g/L-50 g/L of a quenching agent, 3.75 g/L-50 g/L of a quenching agent, 4 g/L-50 g/L of a quenching agent, 4.25 g/L-50 g/L of a quenching agent, 4.5 g/L-50 g/L of a quenching agent, 4.75 g/L-50 g/L of a quenching agent, 5 g/L-50 g/L of a quenching agent, 5.25 g/L-50 g/L of a quenching agent, 5.5 g/L-50 g/L of a quenching agent, 5.75 g/L-50 g/L of a quenching agent, 6 g/L-50 g/L of a quenching agent, 6.25 g/L-50 g/L of a quenching agent, 6.5 g/L-50 g/L of a quenching agent, 6.75 g/L-50 g/L of a quenching agent, 7 g/L-50 g/L of a quenching agent, 7.25 g/L-50 g/L of a quenching agent, 7.5 g/L-50 g/L of a quenching agent, 8 g/L-50 g/L of a quenching agent, 8.25 g/L-50 g/L of a quenching agent, 8.5 g/L-50 g/L of a quenching agent, 8.75 g/L-50 g/L of a quenching agent, 9 g/L-50 g/L of a quenching agent, 9.25 g/L-50 g/L of a quenching agent, 9.5 g/L-50 g/L of a quenching agent, 9.75 g/L-50 g/L of a quenching agent, 10 g/L-50 g/L of a quenching agent, 10.25 g/L-50 g/L of a quenching agent, 10.5 g/L-50 g/L of a quenching agent, 10.75 g/L-50 g/L of a quenching agent, 11 g/L-50 g/L of a quenching agent, 11.25 g/L-50 g/L of a quenching agent, 11.5 g/L-50 g/L of a quenching agent, 11.75 g/L-50 g/L of a quenching agent, 12 g/L-50 g/L of a quenching agent, 12.25 g/L-50 g/L of a quenching agent, 12.5 g/L-50 g/L of a quenching agent, 12.75 g/L-50 g/L of a quenching agent, 13 g/L-50 g/L of a quenching agent, 13.25 g/L-50 g/L of a quenching agent, 13.5 g/L-50 g/L of a quenching agent, 13.75 g/L-50 g/L of a quenching agent, 14 g/L-50 g/L of a quenching agent, 14.25 g/L-50 g/L of a quenching agent, 14.5 g/L-50 g/L of a quenching agent, 14.75 g/L-50 g/L of a quenching agent, 15 g/L-50 g/L of a quenching agent, 2.5 g/L-40 g/L of a quenching agent, 5 g/L-40 g/L of a quenching agent, 7.5 g/L-40 g/L of a quenching agent, 10 g/L-40 g/L of a quenching agent, 12.5 g/L-40 g/L of a quenching agent, 15 g/L-40 g/L of a quenching agent, 1.75 g/L-40 g/L of a quenching agent, 2 g/L-40 g/L of a quenching agent, 2.25 g/L-40 g/L of a quenching agent, 2.5 g/L-40 g/L of a quenching agent, 2.75 g/L-40 g/L of a quenching agent, 3 g/L-40 g/L of a quenching agent, 3.25 g/L-40 g/L of a quenching agent, 3.5 g/L-40 g/L of a quenching agent, 3.75 g/L-40 g/L of a quenching agent, 4 g/L-40 g/L of a quenching agent, 4.25 g/L-40 g/L of a quenching agent, 4.5 g/L-40 g/L of a quenching agent, 4.75 g/L-40 g/L of a quenching agent, 5 g/L-40 g/L of a quenching agent, 5.25 g/L-40 g/L of a quenching agent, 5.5 g/L-40 g/L of a quenching agent, 5.75 g/L-40 g/L of a quenching agent, 6 g/L-40 g/L of a quenching agent, 6.25 g/L-40 g/L of a quenching agent, 6.5 g/L-40 g/L of a quenching agent, 6.75 g/L-40 g/L of a quenching agent, 7 g/L-40 g/L of a quenching agent, 7.25 g/L-40 g/L of a quenching agent, 7.5 g/L-40 g/L of a quenching agent, 8 g/L-40 g/L of a quenching agent, 8.25 g/L-40 g/L of a quenching agent, 8.5 g/L-40 g/L of a quenching agent, 8.75 g/L-40 g/L of a quenching agent, 9 g/L-40 g/L of a quenching agent, 9.25 g/L-40 g/L of a quenching agent, 9.5 g/L-40 g/L of a quenching agent, 9.75 g/L-40 g/L of a quenching agent, 10 g/L-40 g/L of a quenching agent, 10.25 g/L-40 g/L of a quenching agent, 10.5 g/L-40 g/L of a quenching agent, 10.75 g/L-40 g/L of a quenching agent, 11 g/L-40 g/L of a quenching agent, 11.25 g/L-40 g/L of a quenching agent, 11.5 g/L-40 g/L of a quenching agent, 11.75 g/L-40 g/L of a quenching agent, 12 g/L-40 g/L of a quenching agent, 12.25 g/L-40 g/L of a quenching agent, 12.5 g/L-40 g/L of a quenching agent, 12.75 g/L-40 g/L of a quenching agent, 13 g/L-40 g/L of a quenching agent, 13.25 g/L-40 g/L of a quenching agent, 13.5 g/L-40 g/L of a quenching agent, 13.75 g/L-40 g/L of a quenching agent, 14 g/L-40 g/L of a quenching agent, 14.25 g/L-40 g/L of a quenching agent, 14.5 g/L-40 g/L of a quenching agent, 14.75 g/L-40 g/L of a quenching agent, or 15 g/L-40 g/L of a quenching agent.

The urine collection sample of the disclosure may also be pre-packed with a chelating reagent. A chelator, or chelating reagent, is a chemical that binds and holds on to (chelates) minerals and metals such as chromium, iron, lead, mercury, copper, aluminum, nickel, zinc, calcium, cobalt, manganese, and magnesium. The urine collection tube of the disclosure can be packed with a chelator such as diethylenetriaminepentaaceic acid (DTPA; $C_{14}H_{23}O_{10}N_3$), ethylenediaminetetraacetic acid (EDTA; $C_{10}H_{16}O_8N_2$), cyclohexaneediaminetetraacetic acid (CDTA; $C_{14}H_{22}O_8N_2$), ethylenediaminedi-o-hydroxuphenylacetic acid (EDDHA;

$C_{18}H_{20}O_8N_2$), hydroxyethylethylenediaminetriacetic acid (HEDTA; $C_{10}H_{18}O_7N_2$), nitrilotriacetic acid (NTA; $C_6H_9O_6N$), ethylene glycol bis (2-aminoethyl ether) tetraacetic acid (EGTA; $C_{14}H_{24}O_{10}N_2$), citric acid (CIT; $C_6H_2O_4$), oxalic acid (OX; $C_2H_2O_4$), pyrophosphoric acid ($P_2O_7$; $H_4P_2O_7$), and triphosphoric acid ($P_3O_{10}$; $H_5P_3O_{10}$). A urine collection tube of the disclosure may be pre-packed with anywhere from: 1 mM to 500 mM of a chelating agent, 1 mM to 490 mM of a chelating agent, 1 mM to 480 mM of a chelating agent, 1 mM to 470 mM of a chelating agent, 1 mM to 460 mM of a chelating agent, 1 mM to 450 mM of a chelating agent, 1 mM to 440 mM of a chelating agent, 1 mM to 430 mM of a chelating agent, 1 mM to 420 mM of a chelating agent, 1 mM to 410 mM of a chelating agent, 1 mM to 400 mM of a chelating agent, 1 mM to 390 mM of a chelating agent, 1 mM to 380 mM of a chelating agent, 1 mM to 370 mM of a chelating agent, 1 mM to 360 mM of a chelating agent, 1 mM to 350 mM of a chelating agent, 1 mM to 340 mM of a chelating agent, 1 mM to 330 mM of a chelating agent, 1 mM to 320 mM of a chelating agent, 1 mM to 310 mM of a chelating agent, 1 mM to 300 mM of a chelating agent, 1 mM to 290 mM of a chelating agent, 1 mM to 280 mM of a chelating agent, 1 mM to 270 mM of a chelating agent, 1 mM to 260 mM of a chelating agent, 1 mM to 250 mM of a chelating agent, 1 mM to 240 mM of a chelating agent, 1 mM to 230 mM of a chelating agent, 1 mM to 220 mM of a chelating agent, 1 mM to 210 mM of a chelating agent, 1 mM to 200 mM of a chelating agent, 1 mM to 190 mM of a chelating agent, 1 mM to 180 mM of a chelating agent, 1 mM to 170 mM of a chelating agent, 1 mM to 160 mM of a chelating agent, 1 mM to 150 mM of a chelating agent, 1 mM to 140 mM of a chelating agent, 1 mM to 130 mM of a chelating agent, 1 mM to 120 mM of a chelating agent, 1 mM to 110 mM of a chelating agent, 1 mM to 100 mM of a chelating agent, 1 mM to 90 mM of a chelating agent, 1 mM to 80 mM of a chelating agent, 1 mM to 70 mM of a chelating agent, 1 mM to 60 mM of a chelating agent, 1 mM to 50 mM of a chelating agent, 1 mM to 40 mM of a chelating agent, 10 mM to 100 mM of a chelating agent, 20 mM to 100 mM of a chelating agent, 30 mM to 100 mM of a chelating agent, 40 mM to 100 mM of a chelating agent, 50 mM to 100 mM of a chelating agent, 60 mM to 100 mM of a chelating agent, 70 mM to 100 mM of a chelating agent, 10 mM to 150 mM of a chelating agent, 20 mM to 150 mM of a chelating agent, 30 mM to 150 mM of a chelating agent, 40 mM to 150 mM of a chelating agent, 50 mM to 150 mM of a chelating agent, 60 mM to 150 mM of a chelating agent, or 70 mM to 150 mM of a chelating agent.

In preferred instances, each collection tube in the kit is pre-packed with the formaldehyde, the quenching solution, the chelator, and a suitable amount of sodium azide to prevent bacterial growth in the tube. The volume of the pre-packaged solution can range from 0.5 milliliters to 4 milliliters depending on the size of the collection tube. Such amounts provide for a concentrated amount of formaldehyde+quenching solution+chelator that is generally diluted about 5-fold by the addition of the urine sample when the subject attaches the urine collection tube to the vacutainer. In many instances, an excess amount of a formaldehyde+quenching solution+chelator as provided in a vacutainer of the disclosure does not affect the ability of the particular biomarker to be further analyzed, but a minimum amount of preservative is required. Pre-packaging in the vacutainers of the disclosure provides a suitable amount of a formaldehyde+quenching solution+chelator for combining with a volume of urine that is in the range of 1 mL to 20 mLs; in the range of 1 mL to 15 mLs; in the range of 1 mL to 10 mLs; in the range of 1 mL to 5 mLs; or another suitable amounts within those ranges.

Further, in addition to cfDNA, the solution describes above also stabilizes methylated cfDNA. DNA methylation is a common epigenetic modification achieved by adding a methyl group to the fifth carbon of cytosine (5-methylcytosine, 5 mC) via DNA methyltransferases (DNMTs). The current human genome build contains about 28 million CpGs, 60-80% of which are methylated. Generally, the majority of all CpGs are methylated in human, except short unmethylated regions called CpG islands (CGIs). Thus, methylated cfDNA can also be a biomarker for the presence of cfDNA in a sample.

In addition, methylation patterns of cfDNA can be consistent with their originated cells or tissues. Since circulating nucleic acids can originate from different tissues, including an allograft, unique methylation patterns can be used to distinguish cfDNA originated from donor as compared to recipient. For instance, bisulfite sequencing (also known as bisulphite sequencing) is the use of bisulfite treatment of DNA before routine sequencing to determine the pattern of methylation. Treatment of DNA with bisulfite converts cytosine residues to uracil, but leaves 5-methylcytosine residues unaffected. Therefore, DNA that has been treated with bisulfite retains only methylated cytosines. Thus, bisulfite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information. Thus, such an analysis can differentiate between single nucleotide polymorphisms from allograft cfDNA (cytosines and thymidine) as compared to single nucleotides polymorphisms from the recipient of the transplant.

The disclosure provides kits and methods that effectively collect and preserve cfDNA, including methylated forms of cfDNA, and protein for an analysis that may occur several days after sample collection. Thus, the kits of the disclosure have included various pre-analytical factors such as the type of urine collection tubes, ease of collection by an unassisted subject (e.g., subject at home without certified healthcare assistance), sample storage conditions (temperatures for home storage and shipping of samples via a courier service) and easy to follow protocol to increase compliance with a monitoring regimen. In some cases, the solutions describe herein provide a urine sample where the cfDNA and most proteins (total protein) are stable for at least 5 days, at least 6 days, at least 7 days, at least 8 days, at least 9 days, or at least 10 days at room temperature. Such stability provides an unprecedent ability for the subject to collect the urine sample at his/her own dwelling and ship it to a laboratory for subsequent analysis.

Stabilizing Urine Biomarkers in Collection Tubes of the Disclosed Kits

C-X-C Motif Ligands, clusterin, and Creatine Collection Tubes

In some cases, a kit of the disclosure has a second urine collection tube that is also pre-packaged with a stabilizing solution. In some cases, the cell free DNA may not be stable in the second urine collection tube. Preferably, the second urine collection tube comprises a chelator, a polyol, and sodium azide in a concentration sufficient to inhibit nucleases, cell lysis, and bacterial growth in the sample.

Chemokines and their corresponding receptors serve as inflammatory and migratory signals for immune cells.

Examples of these include CXCR3 and its corresponding ligands, CXCL9, CXCL10 and CXCL11, which participate in the induction of immune responses against several foreign antigens. Because renal allograft recipients are at continuous risk for numerous adverse conditions, including alloimmune rejection, detection of a rise inflammatory markers that threaten the long-term survival of the allograft can help identify organ rejection.

CXCL10 has been well established as a marker of immune-mediated injury in a variety of contexts due to its role as a ligand for the CXCR3 receptor. CXCL10 and cfDNA have also been shown to detect chronic lung allograft dysfunction in lung transplantation as well as rejection in kidney transplantation. Recent studies found that there is a significant number of patients with traditionally non-immune kidney diseases, such as hypertension and type 2 diabetes, that had elevated CXCL10, potentially indicating a broader utility in the detection of early-stage kidney injury. Prior studies have identified type 2 diabetes to have a significant CXCL10-mediated component and have identified endothelial cell-produced CXCL10 as a contributor to essential hypertension.

Clusterin, a glycoprotein with potent cohesive properties, is induced in a wide variety of acute and chronic experimental renal diseases. Clusterin mRNA is found in almost all mammal tissues and is constitutively expressed in epithelial and neuronal cells, mainly at the interface of fluid-tissue boundary of biologically active fluids including digestive juice, semen, urine, cerebrospinal fluid (CSF), and plasma/serum. Clusterin mRNA and protein expression are regulated during development and pathophysiologic processes and appear to be involved in a variety of stress responses as a biomarker of cellular senescence. Yet, on its own, clusterin has proved to be an insufficient and unreliable marker of renal damage, particularly allograft damage.

Creatinine is a waste product produced by muscles from the breakdown of a compound called creatine. Creatinine is removed from the body by the kidneys. It is released at a constant rate by the body (depending on muscle mass). Thus urinary creatinine is an index of muscle mass when kidney function is normal. It is increased in body protein breakdown (catabolism), as in trauma and surgery. One gram of urinary creatinine is equivalent to about 17 to 20 kg body mass.

Symmetric dimethylarginine (SDMA) is a sensitive circulating kidney biomarker whose concentrations in urine are believe to increase earlier than creatinine as glomerular filtration rate decreases. Unlike creatinine, SDMA is also believed to be unaffected by lean body mass. It has been studied in canine blood for early detection of decreasing kidney function in canines with chronic kidney disease (CKD).

ADMA is a metabolic by-product of continual protein modification processes in the cytoplasm of all human cells. It is closely related to L-arginine, a conditionally essential amino acid. ADMA interferes with L-arginine in the production of nitric oxide (NO), a key chemical involved in normal endothelial function and, by extension, cardiovascular health.

The second urine collection sample of the disclosure may be pre-packed with a polyol, such as polyethylene glycol (PEG), glycerol, vaseline, or another suitable polyol. The concentration of the polyol in the second urine collection tube may be at least 40%, at least 50%, at least 60%, or at least 65% percent of the volume in the pre-packed second tube.

The second urine collection sample of the disclosure may be pre-packed with a chelating reagent. The urine collection tube of the disclosure can also be pre-packed with a chelator such as diethylenetriaminepentaaceic acid (DTPA; $C_{14}H_{23}O_{10}N_3$), ethylenediaminetetraacetic acid (EDTA; $C_{10}H_{16}O_8N_2$), cyclohexaneediaminetetraacetic acid (CDTA; $C_{14}H_{22}O_8N_2$), ethylenediamined-o-hydroxuphenylacetic acid (EDDHA; $C_{18}H_{20}O_8N_2$), hydroxyethylethylenediaminetriacetic acid (HEDTA; $C_{10}H_{18}O_7N_2$), nitrilotriacetic acid (NTA; $C_6H_9O_6N$), ethylene glycol bis (2-aminoethyl ether) tetraacetic acid (EGTA; $C_{14}H_{24}O_{10}N_2$), citric acid (CIT; $C_6H_2O_4$), oxalic acid (OX; $C_2H_2O_4$), pyrophosphoric acid ($P_2O_7$; $H_4P_2O_7$), and triphosphoric acid ($P_3O_{10}$; $H_5P_3O_{10}$). A urine collection tube of the disclosure may be pre-packed with anywhere from: 1 mM to 100 mM of a chelating agent, 1 mM to 90 mM of a chelating agent, 1 mM to 80 mM of a chelating agent, 1 mM to 70 mM of a chelating agent, 1 mM to 60 mM of a chelating agent, 1 mM to 50 mM of a chelating agent, 1 mM to 40 mM of a chelating agent, 10 mM to 100 mM of a chelating agent, 20 mM to 100 mM of a chelating agent, 30 mM to 100 mM of a chelating agent, 40 mM to 100 mM of a chelating agent, 50 mM to 100 mM of a chelating agent, 60 mM to 100 mM of a chelating agent, 70 mM to 100 mM of a chelating agent, 10 mM to 150 mM of a chelating agent, 20 mM to 150 mM of a chelating agent, 30 mM to 150 mM of a chelating agent, 40 mM to 150 mM of a chelating agent, 50 mM to 150 mM of a chelating agent, 60 mM to 150 mM of a chelating agent, or 70 mM to 150 mM of a chelating agent.

In preferred instances, each second collection tube in the kit is pre-packed with the polyol, the chelator, and a suitable amount of sodium azide to prevent bacterial growth in the tube. The volume of the pre-packaged solution can range from 0.5 milliliters to 4 milliliters depending on the size of the collection tube. Such amounts provide for a concentrated amount of formaldehyde+quenching solution+chelator that is generally diluted about 5-fold by the addition of the urine sample when the subject attaches the urine collection tube to the vacutainer.

Using a Kit of the Disclosure to Monitor an Allograft

In most preferred embodiments, a kit and methods of the disclosure can be used to collect and stabilize a combinations of biomarkers for high accuracy monitoring of a solid organ of a subject, such as subject that may have received an allograft during an organ transplant, a subject that donated an allograft—and is otherwise healthy, or a subject that has or is suspected of having a kidney injury, such as a kidney stone, CKD, a kidney injury caused by a virus (e.g., BK virus, Sars-CoV-2).

Following the initial technical challenge of implanting an organ in a transplantation procedure, maintaining the organ against a vast array of pathologies for years to come, remains a challenge for all clinicians working in transplantation. Drug toxicity, opportunistic infection, primary disease recurrence, and the constant battle against organ rejection are all differentials that are considered when graft dysfunction is observed, promoting a lifetime of laborious surveillance.

After organ transplantation, monitoring patients for evidence of rejection is essential for mitigating graft loss. Diagnosis of rejection of solid organ transplants traditionally requires needle biopsy and histological assessment, which in some healthcare models can be costly, logistically challenging and carries the risk of procedure-related complications with associated morbidity. There remains a critical unmet need for an easy to use, non-invasive product, that can provide more than a mere inference of potential allograft injuries, but that is also sensitive enough and accurate enough to eliminate the need for a needle biopsy or histological assessment.

There are multiple challenges in requiring the recipient of an allograft to frequently be submitted to invasive procedures, many of which are exacerbated during pandemic and social restrictions. First, a sample should be obtained in a non-intrusive, or minimally intrusive manner. Second, the sample must be a source of informative biomarkers for monitoring transplant health and injuries. Third, there is a need for detecting the biomarkers in a reliable, reproducible, and robust manner. Lastly, there is a need for an analysis of the data, which can require transforming data obtained by quantitative detection of biomarkers to create a composite score for a condition being studied, e.g. acute rejection (AR), allograft hypoxia, etc. The kits disclosed here overcome the deficiencies of the current standard-of-care for transplant monitoring, by stabilizing biomarkers for a sufficient period of time after sample collection.

Samples

The terms "biological sample" or "sample" as used herein, refers to a mixture of cells, tissue, and liquids obtained or derived from an individual that contains a cellular and/or other molecular entity that is to be characterized and/or identified, for example based on physical, biochemical, chemical and/or physiological characteristics. In one embodiment the sample is liquid (i.e., a biofluid), such as urine, blood, serum, plasma, saliva, phlegm, etc. In other embodiments, the sample is a histological section, such as a solid tissue section from a biopsy.

Machine Learning Processes

Machine-learning algorithms find and apply patterns in data. Multivariate machine learning, linear and nonlinear fitting algorithms have been applied in biomarker searches. Machine learning is generally supervised or unsupervised. In supervised learning, the most prevalent, the data is labeled to tell the machine exactly what patterns it should look for. For instance, samples of a patient with a known diagnosis of acute rejection are labeled as "acute rejection." Samples from "normal" patients are labeled "normal." The algorithm then starts looking for patterns that are clearly distinct between "normal" and "acute rejection."

In unsupervised learning, the data has no labels. The machine algorithm looks for whatever patterns it can find. This can be interesting if, for instance, every sample analyzed is from a subject who received an allograft. It could, for example, be used for detection of a broad allograft specific marker.

Subjects

A subject can be any human or animal, collectively "individuals", such as a subject that has received an allograft during an organ transplant. For instance, subjects can be humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants. In specific cases, a subject is a pediatric recipient of an allograft.

A "subject", also referred to as an "individual" can be a "patient." A "patient," refers to an subject who is under the care of a treating physician. In one embodiment, the patient is suffering from renal damage or renal injury. In another embodiment, the patient is suffering from renal disease or disorder. In another embodiment, the patient has had a renal transplant and is undergoing of renal graft rejection. In yet other embodiments, the patient has been diagnosed with renal injury, renal disease, or renal graft rejection, but has not had any treatment to address the diagnosis.

Other Definitions

For purposes of interpreting this specification, the following definitions will apply and whenever appropriate, terms used in the singular will also include the plural and vice versa.

"Hybridization", "probe hybridization", "cfDNA probe hybridization" or "Alu probe hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the pairing with a cfDNA sequence (e.g., probe hybridazation to an Alu region of a cfDNA), initiation of PCR, or the cleavage of a polynucleotide by an enzyme. A sequence capable of hybridizing with a given sequence is referred to as the "complement" of the given sequence.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993). Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25 degrees Celsius. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15 degrees Celsius lower than the $T_m$. In order to require at least about 70% nucleotide complementarity of hybridized sequences, moderately-stringent washing conditions are selected to be about 15 to 30 degrees Celsius lower than the $T_m$. Highly permissive (very low stringency) washing conditions may be as low as 50 degrees Celsius below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life-eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component.

As used herein the term "amino acid" includes natural and/or unnatural or synthetic amino acids, including glycine and both the D or L optical isomers, and amino acid analogs and peptidomimetics.

As used herein the term "metabolite" refers to intermediate or end products of metabolism. The term metabolite is usually used for small molecules, but it can also include amino acids, vitamins, nucleotides, antioxidants, organic acids, and vitamins. In preferred cases, the term metabolite refers to creatinine.

As used herein, the term "domain" or "protein domain" refers to a part of a protein sequence that may exist and function independently of the rest of the protein chain.

As used herein, the terms "disorder" or "disease" and "injury" or "damage" are used interchangeably. It refers to any alteration in the state of the body or one of its organs and/or tissues, interrupting or disturbing the performance of organ function and/or tissue function (e.g., causes organ dysfunction) and/or causing a symptom such as discomfort, dysfunction, distress, or even death to a subject afflicted with the disease.

A subject "at risk" of developing renal injury, renal disease or renal graft rejection may or may not have detectable disease or symptoms, and may or may not have displayed detectable disease or symptoms of disease prior to the treatment methods described herein. "At risk" denotes that a subject has one or more risk factors, which are measurable parameters that correlate with development of renal injury, renal disease, or renal graft rejection, as described herein and known in the art. A subject having one or more of these risk factors has a higher probability of developing renal injury, renal disease, or renal graft rejection than a subject without one or more of these risk factor(s).

The term "diagnosis" is used herein to refer to the identification or classification of a medical or pathological state, disease or condition. For example, "diagnosis" may refer to identification of renal injury, renal disease, or renal graft rejection. "Diagnosis" may also refer to the classification of a severity of the renal injury, renal disease, or renal graft rejection. Diagnosis of the renal injury, renal disease, chronic kidney disease (CKD), or renal graft rejection may be made according to any protocol that one of skill of art (e.g., a nephrologist) would use.

The term "companion diagnostic" is used herein to refer to methods that assist in making a clinical determination regarding the presence, degree or other nature, of a particular type of symptom or condition of renal injury, renal disease, or renal graft rejection. For example, a companion diagnostic of renal injury, renal disease, or renal graft rejection can include measuring the fragment size of cell free DNA.

The term "prognosis" is used herein to refer to the prediction of the likelihood of the development and/or recurrence of an injury being treated with an allograft, e.g., a renal injury, renal disease, or renal graft rejection. The predictive methods of the invention can be used clinically to make treatment decisions by choosing the most appropriate treatment modalities for any particular patient. The predictive methods of the present invention are valuable tools in predicting if and/or aiding in the diagnosis as to whether a patient is likely to develop renal injury, renal disease, or renal graft rejection, have recurrence of renal injury, renal disease, or renal graft rejection, and/or worsening of renal injury, renal disease, or renal graft rejection symptoms.

"Treating" and "treatment" refers to clinical intervention in an attempt to alter the natural course of the individual and can be performed before, during, or after the course of clinical diagnosis or prognosis. Desirable effects of treatment include preventing the occurrence or recurrence of renal injury, renal disease, or renal graft rejection or a condition or symptom thereof, alleviating a condition or symptom of renal injury, renal disease, or renal graft rejection, diminishing any direct or indirect pathological consequences of renal injury, renal disease, or renal graft rejection, decreasing the rate of renal injury, renal disease, or renal graft rejection progression or severity, and/or ameliorating or palliating the renal injury, renal disease, or renal graft rejection. In some embodiments, methods and compositions of the invention are used on patient sub-populations identified to be at risk of developing renal injury, renal disease, or renal graft rejection. In some cases, the methods and compositions of the invention are useful in attempts to delay development of renal injury, renal disease, or renal graft rejection. Beneficial or desired clinical results are known or can be readily obtained by one skilled in the art. For example, beneficial or desired clinical results can include, but are not limited to, one or more of the following: monitoring of renal injury, detection of renal injury, identifying type of renal injury, helping renal transplant physicians to decide whether or not to send transplant patients to go for a biopsy and make decisions for the purposes of clinical management and therapeutic intervention.

EXAMPLES

Example 1: Stabilized Cell Free Nucleic Acids in Urine for Shipping Via a Courier Preservation of the integrity of cell free nucleic acids in urine specimens during shipping and handling is crucial for remote monitoring of subjects. An economical and convenient method is described for nucleic acid stabilization by using a protein/nucleic acid stabilizing solution in urine that is designed for the shipment of samples to a laboratory.

A subject receives a kit of the disclosure in the mail, via a courier. The kit comprises two 12 ml urine sample collection tubes pre-packaged with the "first" pre-packaged solution and one 5 ml urine sample collection tube pre-packaged with the "second" pre-packaged solution. the following instructions for use:

1. Prepping the Sample
   A. Take all 12 components out of the box.
   B. Clean genitals with alcohol wipe prior to collecting sample.
2. Collecting the Samples
   A. Insert large tube, with white cap down, into urine collection cup opening and push all the way down for at least 5 seconds. The tube will fill on its own. Remove the tube and flip it back and fourth approximately 10 times. Optionally, the insert instructions will state"
   "Do not remove the white cap on the tube and do not consume the contents of the tube."
   B. Insert 2nd large tube and repeat. Insert small tube and repeat.
   C. Stick one label on each tube.
3. Packaging Samples
   A. Insert the 3 tubes into the white sleeve; sleeve into the biohazard bag; and seal the bag.
   B. Wrap the Therapak gel pack around the biohazard bag and place inside the foil pouch.
   C. Discard remaining urine in toilet and throw sample cup away.
4. Shipping Samples
   Put the foil pouch into your kit box and put the kit box in the provided FedEx shipping bag. Place pre-made shipping label on the FedEx bag.
   Optionally, a subject calls a Transplant Account Specialist to schedule a FedEx pick up

Example 2: Stability of Markers in Solution

Circulating cell-free DNA (cfDNA) in blood plasma derived from tumor, fetus and transplanted organs has been extensively studied. Circulating cfDNA passes from blood, through the kidney barrier, and into urine. However, the inherent instability of cfDNA in urine has previously hindered its clinical utility as a biomarker. Nucleated cells in urine could also release genomic DNA into urine leading to an increased high molecular weight DNA background during sample processing and storage. NephroSant has a urine preservative for stabilizing cfDNA and the other biomarkers that comprise the QSant test in urine.

Preanalytical studies were performed to confirm effective preservative reagent(s) in urine post specimen collection can preserve cfDNA/m-cfDNA, Creatinine, Total Protein, Clusterin and CXCL10 up to 3 days (72 hours) at room temperature (RT). This is essential to ensure stability of clinical specimens during shipment to NephroSant CLIA lab via FedEx overnight priority shipment. The specimen shipper kit included a gel pack that maintains RT during the shipping process.

Briefly, at least one urine sample collection tube having a volume of a pre-packaged solution for stabilizing a biomarker in the urine sample was utilized to stabilize a biomarker in the sample. A first urine collection tube had from 25 g/L-800 g/L of a formaldehyde donor, from 2.5 g/L-80 g/L of a quenching agent, from 1 mM to 500 mM of a chelating agent, and a suitable amount of sodium azide to prevent bacterial growth (optional sodium azide)(Preservative 1). A second urine collection tube was pre-packed with at least 65% percent (volume) of a polyol, from 1 mM to 100 mM of a chelating agent, a crowding reagent such as Bovine Serum Albumin (BSA), and a suitable amount of sodium azide to prevent bacterial growth in the tube (optional sodium azide)(Preservative 3).

Results:

cfDNA and other QSant™ biomarker concentrations remained stable at RT for at least 3 days in urine samples treated with urine preservative.

The disclosure validated urine preservatives that can effectively stabilize urine biomarkers by conducting a time course. The study subjected ~30 patient samples (with high and low native levels) supplemented with a urine preservative and stored for 3 days at RT before testing.

Samples had high and low natural levels of cfDNA/m-cfDNA, Creatinine, Total Protein and Clusterin, but as endogenous levels of CXL10 were very low, a proportion of the samples were spiked with high CXCL10 to cover a higher range of concentration levels. FIGS. 10-14 illustrate the results. Acceptable stability was observed up to 3 days of storage at room temperature.

TABLE 1

QSant Biomarker Stability Study Summary
TABLE 1
Average % Recovery with Preservative

| Biomarker (n samples) | Day 3 |
|---|---|
| cfDNA/m-cfDNA (n = 30) | 102% |
| Clusterin (n = 24) | 87% |
| CXCL10 (n = 26) | 97% |
| Creatinine (n = 29) | 99% |
| Total Protein (n = 28) | 109% |

Percent recovery was calculated for each time-point according to the formula (% Recovery=Observed Concentration Day 3/Observed Concentration Day 0×100%).

Conclusion:

Our results show that addition of a urine preservative stabilizes cfDNA/m-cfDNA, Clusterin, CXCL10, Total Protein and Creatinine in urine for at least 3 days at room temperature. Thus, addition of this preservative will allow for greater sample collection flexibility and reduce preanalytical variation during shipping and sample processing.

Example 3: Urine Preservatives

Circulating cell-free DNA (cfDNA) in blood plasma derived from tumor, fetus and transplanted organs has been extensively studied. Circulating cfDNA passes from blood, through the kidney barrier, and into urine. However, the inherent instability of cfDNA in urine has previously hindered its clinical utility as a biomarker. Nucleated cells in urine could also release genomic DNA into urine leading to an increased high molecular weight DNA background during sample processing and storage.

The disclosure further optimized various alternatives of the urine preservatives lacking the formaldehyde donor described in Example 2, for stabilizing cfDNA and the other biomarkers specifically in urine samples. A second composition was validated that did not require a formaldehyde donor was validated for stabilizing cfDNA and methylated cfDNA. The urine collection tube had from 2.5 g/L-80 g/L of a quenching agent, from 1 mM to 500 mM of a chelating agent, and a suitable amount of sodium azide to prevent bacterial growth (optional) (Preservative 2).

Materials & Equipment

TABLE 2

Exemplary cfDNA reagents used for validation.
TABLE 2

| Manufacturer | Catalog ID | Reagent | Storage Requirement |
|---|---|---|---|
| IDT | Custom | KIT Probe ALU (See, e.g., Sarwal U. S. Pat. No. 11,124,824B2). | −80° C. |
| Promega | Custom | Sonicated Standard Control | −80° C. |
| Invitrogen | AM9625 | 10X PBS | Room Temperature |
| Thermo Fisher Scientific | PI37525 | Blocker BSA (10% in PBS) | Refrigeration (2-8° C.) |
| Thermo Fisher Scientific | 37075 | Super Signal ELISA FEMTO Substrate | Refrigeration (2-8° C.) |
| R&D Systems | DY998 | Streptavidin HRP | Refrigeration (2-8° C.) |
| Greiner | 655074 | LUMITRAC 600 HB microplate 96 well | Room Temperature |
| Thermo Fisher Scientific | DY992 | ELISA Plate Sealers | Room Temperature |
| VistaLab Tech. | 21381090 | Reservoir | Room Temperature |

TABLE 3 m-cfDNA reagents used for validation.
TABLE 3

| Manufacturer | Catalog ID | Reagent | Storage Requirement |
|---|---|---|---|
| Thermo Fisher Scientific | MA5-24694 | 5-Methylcytosine Recombinant Rabbit Monoclonal Antibody (RM231) | ≤−20° C. |
| Thermo Fisher Scientific | 32260 | Goat anti-Rabbit Poly HRP Secondary Antibody | Refrigeration (2-8° C.) |
| In-house | N/A | sfmDNA Standard | ≤−20° C. |
| Invitrogen | AM9625 | 10X PBS | Room Temperature |
| Thermo Fisher Scientific | PI37525 | Blocker BSA (10% in PBS) | Refrigeration (2-8° C.) |
| Thermo Fisher Scientific | 37075 | Super Signal ELISA Femto Substrate | Refrigeration (2-8° C.) |

TABLE 3-continued m-cfDNA reagents used for validation.

| Manufacturer | Catalog ID | Reagent | Storage Requirement |
|---|---|---|---|
| R&D Systems | DY998 | Streptavidin HRP | Refrigeration (2-8° C.) |
| Greiner | 655074 | LUMITRAC 600 HB microplate 96 well | Room Temperature |
| Thermo Fisher Scientific | DY992 | ELISA Plate Sealers | Room Temperature |
| VistaLab Tech. | 21381090 | Reservoir | Room Temperature |

TABLE 4

Extraction reagents for QIASymphony.

| Manufacturer | Catalog ID | Reagent | Storage Requirement |
|---|---|---|---|
| Qiagen | 55114 | QIAamp Circulating Nucleic Acid kit | Room Temperature |
| Qiagen | | **QIAGEN Mini Columns | Room Temperature |
| Qiagen | | **Tube extenders (20 mL) | Room Temperature |
| Qiagen | | **Collection tubes (2.0 mL) | Room Temperature |
| Qiagen | | **Elution tubes (1.5 mL) | Room Temperature |
| Qiagen | | **VacConnectors | Room Temperature |
| Qiagen | | **Buffer ACL | Room Temperature |
| Qiagen | | **Buffer ACB | Room Temperature |
| Qiagen | | **Buffer ACW1 | Room Temperature |
| Qiagen | | **Buffer ACW2 | Room Temperature |
| Qiagen | | **Buffer AVE | Room Temperature |
| Qiagen | | **QIAGEN Proteinase K | Refrigeration (2-8° C.) |
| Qiagen | | **Carrier RNA | Room Temperature |
| Qiagen | 939016 | Buffer ATL | Room Temperature |
| Fisher Chemical | A4094 | Ethanol | Room Temperature |
| Fisher Chemical | A416P4 | Isopropanol | Room Temperature |

TABLE 4

Extraction reagents for QIASymphony ™.

| | | | cfDNA | | |
|---|---|---|---|---|---|
| Sample | Treatment | Timepoint | Avg RLU | Avg Conc. (GE/mL) | % Recovery |
| NUP383 | Preservative 1 | Day 0 | 5,880,121 | 1,472.19 | 100% |
| | | Day 1 | 6,886,189 | 1,729.98 | 118% |
| | | Day 4 | 6,503,755 | 1,631.98 | 111% |
| | Preservative 2 | Day 0 | 4,346,558 | 1,079.23 | 100% |
| | | Day 1 | 6,646,464 | 1,668.55 | 155% |
| | | Day 4 | 8,306,339 | 2,093.87 | 194% |
| NUP384 | Control (No Preservative) | Day 0 | 610,625 | 121.96 | 100% |
| | | Day 3 | 337,367 | 51.94 | 43% |
| | Preservative 1 | Day 0 | 1,442,210 | 335.04 | 100% |
| | | Day 3 | 28,098,385 | 7,165.29 | 2139% |
| | Preservative 2 | Day 0 | 5,736,603 | 1,435.41 | 100% |
| | | Day 3 | 99,112 | −9.11 | −1% |
| NUP385 | Control (No Preservative) | Day 0 | 37,820,221 | 9,656.37 | 100% |
| | | Day 3 | 82,174 | −13.45 | 0% |
| | Preservative 1 | Day 0 | 101,691 | −8.45 | 100% |
| | | Day 3 | 11,548,671 | 2,924.67 | −34611% |
| | Preservative 2 | Day 0 | 368,572 | 59.93 | 100% |
| | | Day 3 | 13,553,054 | 3,438.26 | 5737% |
| NUP386 | Control (No Preservative) | Day 0 | 153,960 | 4.94 | 100% |
| | | Day 3 | 883,897 | 191.98 | 3886% |
| | Preservative 1 | Day 0 | 370,242 | 60.36 | 100% |
| | | Day 3 | 4,906,278 | 1,222.65 | 2026% |
| | Preservative 2 | Day 0 | 3,594,331 | 886.49 | 100% |
| | | Day 3 | 5,539,602 | 1,384.93 | 156% |
| NUP387 | Control (No Preservative) | Day 0 | 133,955 | 11.44 | 100% |
| | | Day 3 | 99,443 | 3.68 | 32% |

TABLE 4-continued

Extraction reagents for QIASymphony ™.
TABLE 4

| Sample | Treatment | Timepoint | cfDNA Avg RLU | Avg Conc. (GE/mL) | % Recovery |
|---|---|---|---|---|---|
|  | Preservative 1 | Day 0 | 83,728 | 0.14 | 100% |
|  |  | Day 3 | 439,915 | 80.25 | 57321% |
|  | Preservative 2 | Day 0 | 66,165 | −3.81 | 100% |
|  |  | Day 3 | 726,278 | 144.66 | −3797% |
| NUP388 | Control (No Preservative) | Day 0 | 50,290 | −7.38 | 100% |
|  |  | Day 3 | 125,388 | 9.51 | −129% |
|  | Preservative 1 | Day 0 | 60,230 | −5.14 | 100% |
|  |  | Day 3 | 284,591 | 45.32 | −882% |
|  | Preservative 2 | Day 0 | 91,016 | 1.78 | 100% |
|  |  | Day 3 | 509,108 | 95.82 | 5383% |
| NUP389 | Control (No Preservative) | Day 0 | 3,048,123 | 666.86 | 100% |
|  |  | Day 3 | 4,430,467 | 977.77 | 147% |
|  | Preservative 1 | Day 0 | 10,042,712 | 2,240.01 | 100% |
|  |  | Day 3 | 10,281,310 | 2,293.68 | 102% |
|  | Preservative 2 | Day 0 | 7,974,249 | 2,183.71 | 100% |
|  |  | Day 3 | 11,577,127 | 2,585.12 | 118% |

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A kit for the stabilization of a urine sample from a subject comprising:
   a cup having a lid for the collection of the urine sample from the subject, the cup lid having an inner protrusion for insertion of a urine sample collection tube therein, the inner protrusion having a piercing hollow channel; and
   two or more urine sample collection tubes, wherein
      a first urine sample collection tube of the two or more urine sample collection tubes comprises a first a stabilization solution comprising 2.5 g/L to 80 g/L of a quenching agent and 1 mM to 500 mM of a first chelator contained within the first urine sample collection tube contained within the first urine sample collection tube by a first top that is pierceable by the piercing hollow channel when pressed against the lid of the cup having the piercing hollow channel therein;
      a second urine collection tube of the two or more urine sample collection tubes, comprises a second stabilization solution comprising 1 mM to 100 mM of a second chelator and at least 65% (volume) of a polyol contained within the second urine sample collection tube by a second top that is pierceable by the piercing hollow channel when pressed against the lid of the cup having the piercing hollow channel therein;
   an envelope, a box, or a bag for shipping the two or more urine sample collection tubes after urine collection via a courier service.

2. The kit of claim 1, wherein the first stabilization solution stabilizes cfDNA at temperatures up to 86° F. in the first urine sample collection tubes.

3. The kit of claim 1, wherein the kit comprises a third urine sample collection tube.

4. The kit of claim 3, wherein the third urine sample collection tube comprises a volume of a pre-packaged solution, a pre-packaged powder, or a pre-packaged gel for stabilizing at least one biomarker.

5. The kit of claim 1, wherein the second stabilization solution stabilizes an inflammation marker in the urine sample.

6. The kit of claim 5, wherein the inflammation marker is CXCL10 or CXCL9.

7. The kit of claim 1, wherein the second stabilization solution stabilizes an apoptotic marker in the urine sample.

8. The kit of claim 7, wherein the apoptotic marker is clusterin.

9. The kit of claim 1, wherein the second stabilization solution stabilizes a metabolite in the urine sample.

10. The kit of claim 9, wherein the metabolite is creatinine.

11. The kit of claim 1, wherein the envelope, the box, or the bag are pre-addressed for postage to a urine analysis laboratory via the courier service.

12. The kit of claim 11, wherein the postage to the urine analysis laboratory is pre-paid.

13. The kit of claim 1, wherein the volume of the first stabilization solution in the first urine collection tube ranges from 0.5 milliliters to 4 milliliters.

14. The kit of claim 1, wherein the volume of the first stabilization solution provides for a 5 fold dilution of the urine sample.

15. The kit of claim 1, wherein one or both of the two or more urine sample collection tubes is a 5 milliliter collection tube, a 10 milliliter collection tube, or a 12 milliliter collection tube.

16. The kit of claim 1, wherein the subject has received an allograft.

17. The kit of claim 16, wherein the allograft is kidney allograft.

18. The kit of claim 1, wherein the second stabilizing solution does not stabilize cfDNA in the second urine collection tube.

* * * * *